(12) United States Patent
Doucey et al.

(10) Patent No.: US 10,858,626 B2
(45) Date of Patent: Dec. 8, 2020

(54) ADOPTIVE IMMUNOTHERAPY FOR TREATING CANCER

(71) Applicant: UNIVERSITÉ DE LAUSANNE, Lausanne (CH)

(72) Inventors: Marie-Agnes Doucey, Lausanne (CH); Nicolas Guex, Lausanne (CH); Isaac Crespo, Lausanne (CH); Ioannis Xenarios, Lausanne (CH)

(73) Assignee: UNIVERSITÉ DE LAUSANNE, Lausanne (CH)

( * ) Notice: Subject to any disclaimer, the term of this patent is extended or adjusted under 35 U.S.C. 154(b) by 96 days.

(21) Appl. No.: 15/536,258

(22) PCT Filed: Dec. 15, 2015

(86) PCT No.: PCT/EP2015/079867
§ 371 (c)(1),
(2) Date: Jun. 15, 2017

(87) PCT Pub. No.: WO2016/096903
PCT Pub. Date: Jun. 23, 2016

(65) Prior Publication Data
US 2017/0349880 A1    Dec. 7, 2017

(30) Foreign Application Priority Data

Dec. 17, 2014 (EP) .................... 14198399

(51) Int. Cl.
| | | |
|---|---|---|
| A61K 31/00 | (2006.01) |
| C12N 5/0783 | (2010.01) |
| A61K 39/00 | (2006.01) |
| A61K 31/444 | (2006.01) |
| A61K 31/4709 | (2006.01) |
| A61K 31/496 | (2006.01) |
| A61K 31/502 | (2006.01) |
| A61K 31/517 | (2006.01) |
| A61K 31/5377 | (2006.01) |
| A61K 45/06 | (2006.01) |
| A61K 31/404 | (2006.01) |
| A61K 31/44 | (2006.01) |
| A61K 31/5025 | (2006.01) |
| A61K 31/506 | (2006.01) |
| A61K 31/4439 | (2006.01) |
| A61K 31/47 | (2006.01) |
| A61K 31/4365 | (2006.01) |

(52) U.S. Cl.
CPC .......... *C12N 5/0636* (2013.01); *A61K 31/404* (2013.01); *A61K 31/4365* (2013.01); *A61K 31/44* (2013.01); *A61K 31/444* (2013.01); *A61K 31/4439* (2013.01); *A61K 31/47* (2013.01); *A61K 31/4709* (2013.01); *A61K 31/496* (2013.01); *A61K 31/502* (2013.01); *A61K 31/506* (2013.01); *A61K 31/5025* (2013.01); *A61K 31/517* (2013.01); *A61K 31/5377* (2013.01); *A61K 39/0011* (2013.01); *A61K 45/06* (2013.01); *C12N 5/0638* (2013.01); *A61K 2039/5158* (2013.01); *C12N 2501/165* (2013.01); *C12N 2501/17* (2013.01)

(58) Field of Classification Search
CPC .............................. C12N 5/0636; A61K 31/00
USPC ....................................... 424/132.1
See application file for complete search history.

(56) References Cited

U.S. PATENT DOCUMENTS

2015/0250864 A1\* 9/2015 Wang-Johanning ........................
A61K 39/12
424/204.1

OTHER PUBLICATIONS

Chacon J. et al., (2014) "Manipulating the Tumor Microenvironment Ex Vivo for Enhanced Expansion of Tumor-Infiltrating Lymphocytes for Adoptive Cell Therapy" Clinical Cancel Research 21:3 pp. 611-621.
Ibberson M. et al., (2013) "TIE-2 and VEGFR Kinase Activities Drive Immunosuppressive Function of TIE-2-Expressing Monocytes in Human Breast Tumors" Clinical Cancer Research 19:13 pp. 3439-3449.
International Search Report dated Feb. 29, 2016 issued in International Patent Application No. PCT/EP2015/079867.
Ye Q. et al., (2013) "CD137 Accurately Identifies and Enriches for Naturally Occurring Tumor-Reactive T Cells in Tumor" Clinical Cancer Research 20:1 pp. 44-55.

\* cited by examiner

*Primary Examiner* — Yan Xiao
(74) *Attorney, Agent, or Firm* — Harness Dickey & Pierce P.L.C.

(57) ABSTRACT

The present invention provides methods for producing and/or expanding tumor-infiltrating lymphocytes (TILs) that can be used in adoptive immunotherapy in cancer treatment.

7 Claims, 14 Drawing Sheets

Fig. 1 A & B
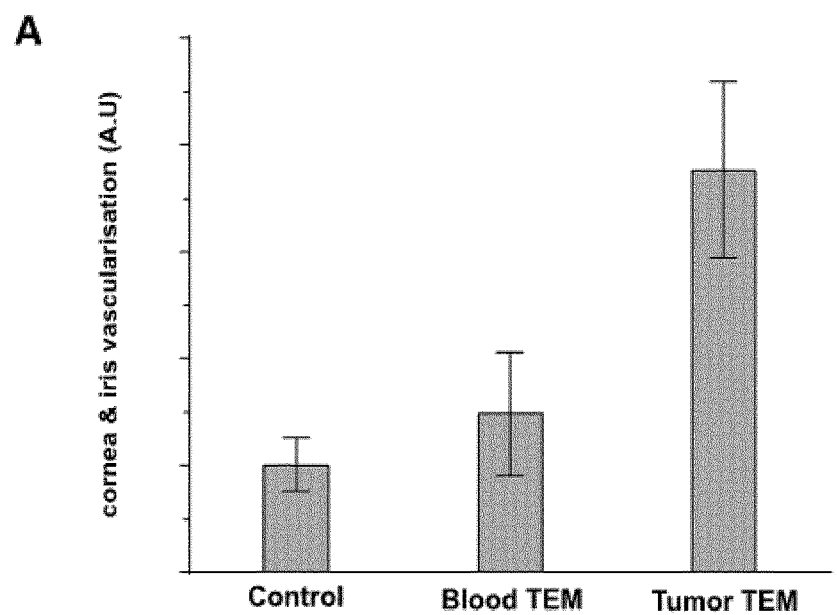
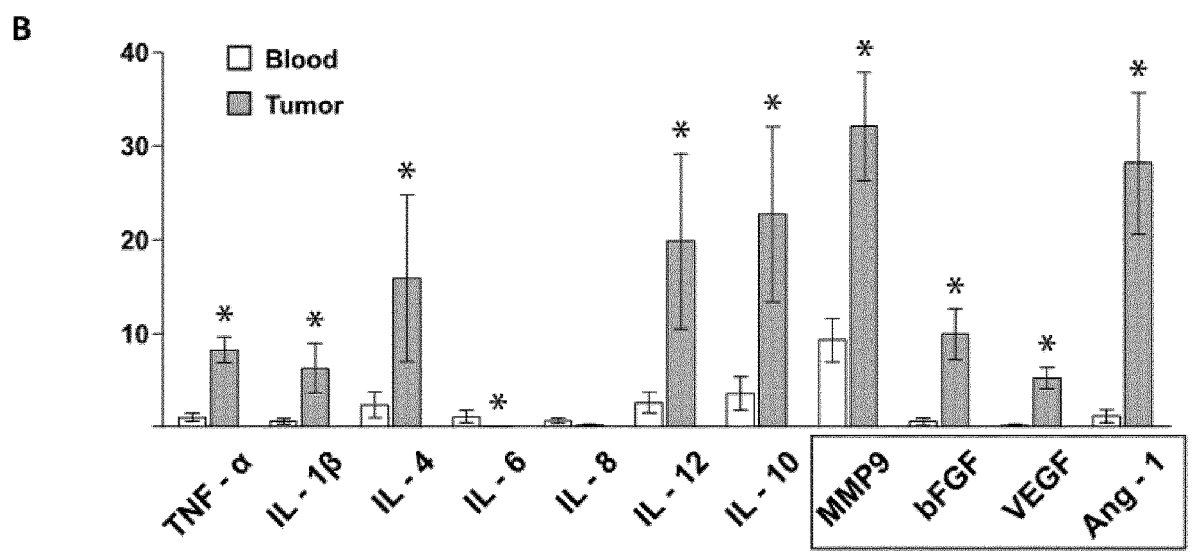

Fig. 1 C
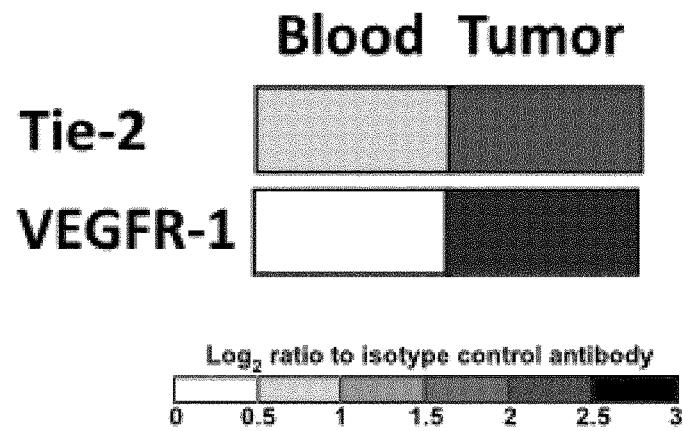
Fig. 2 A & B
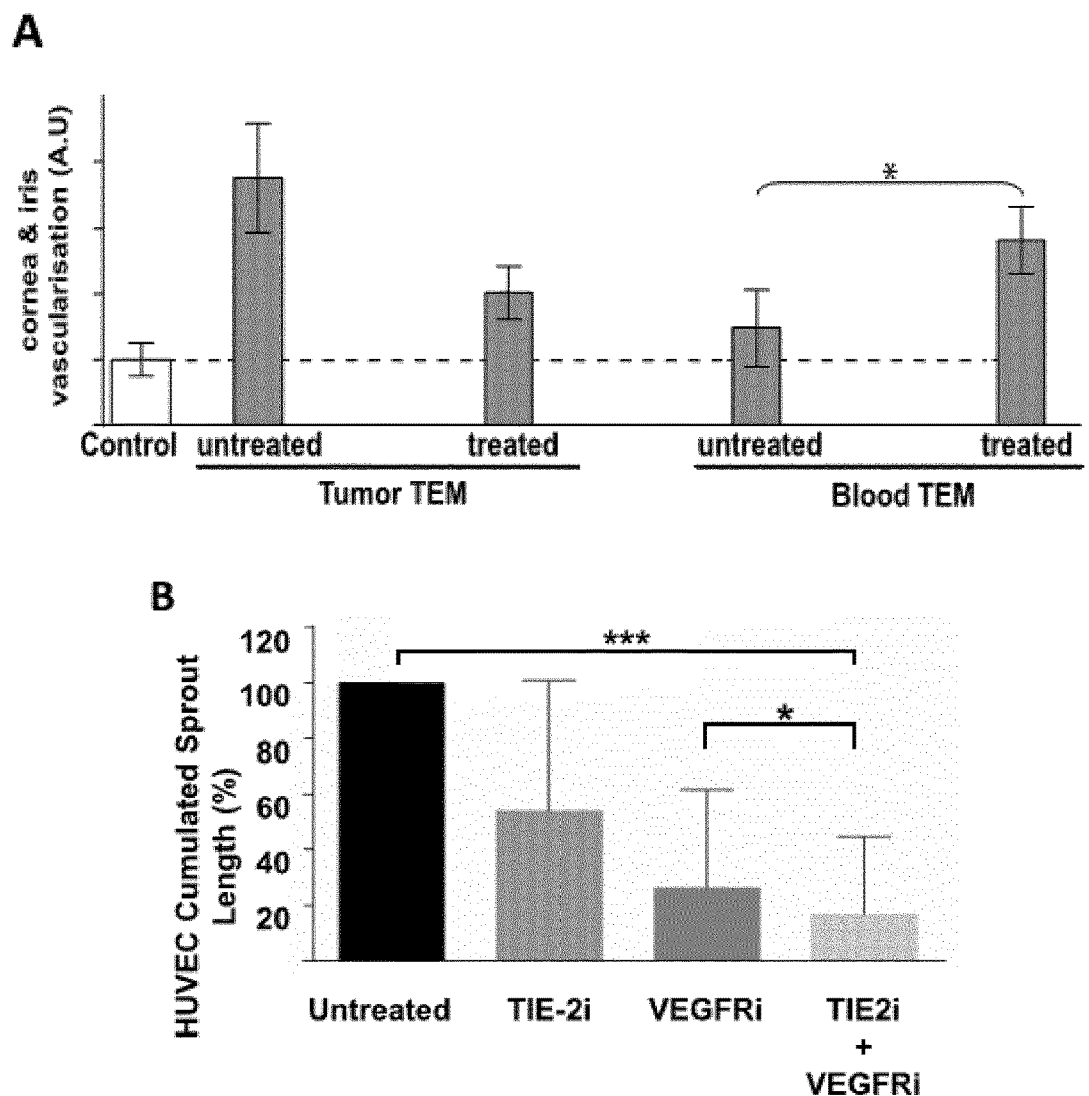

Fig. 2 C & D
C
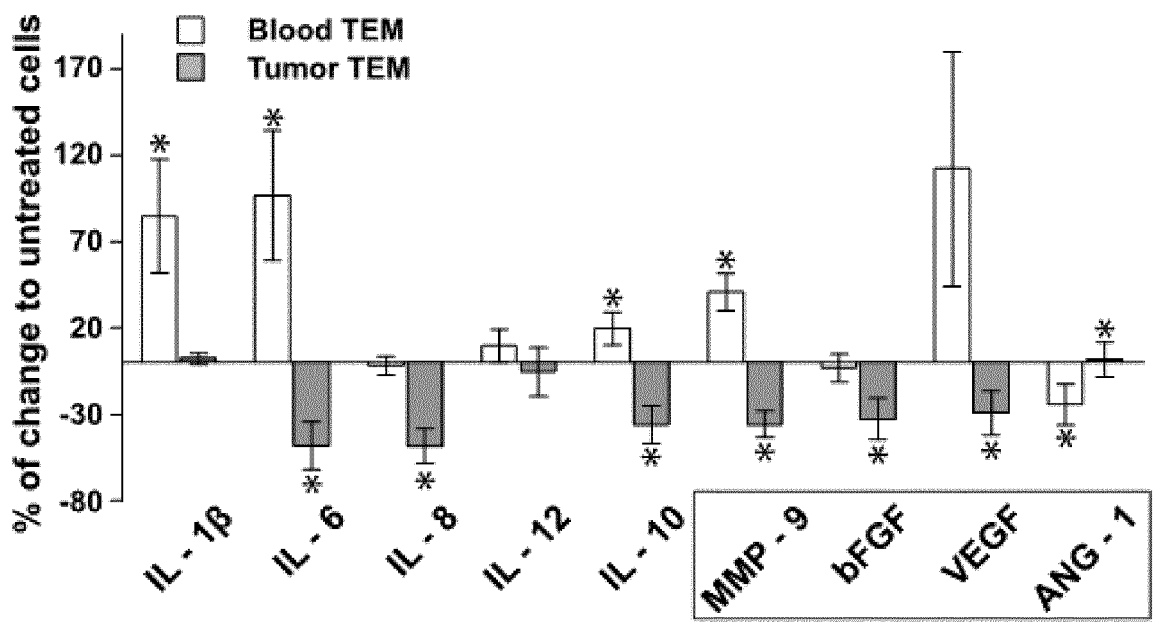
D
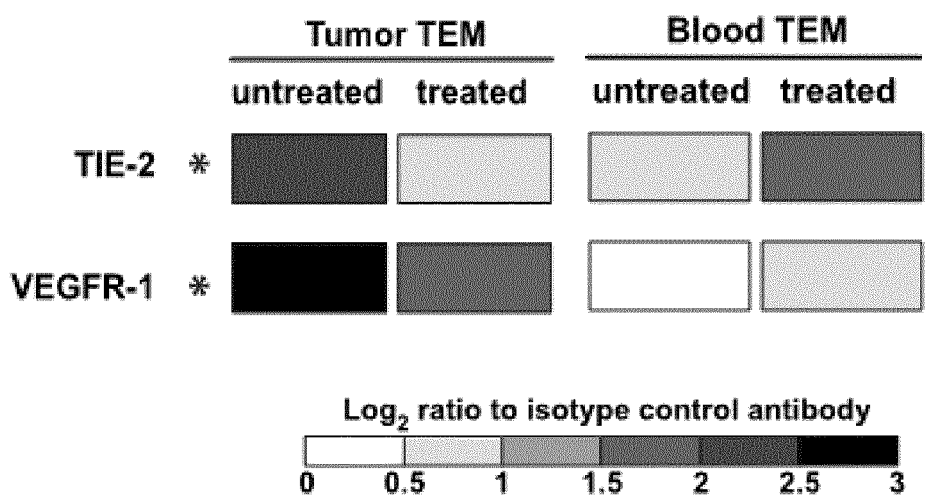

Fig. 3 B
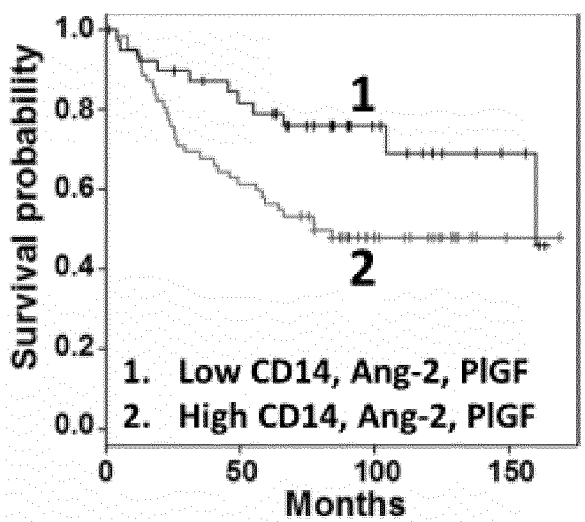
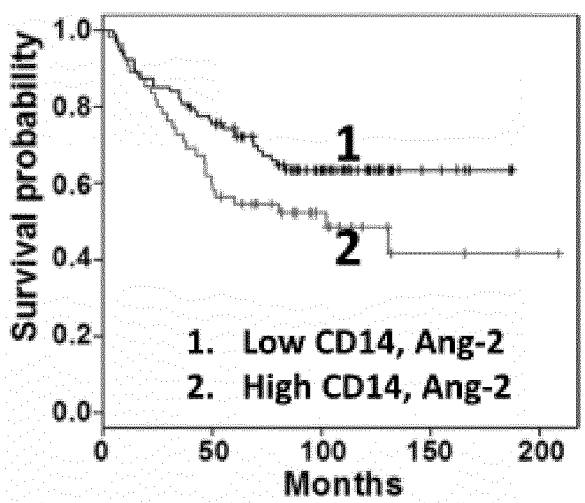
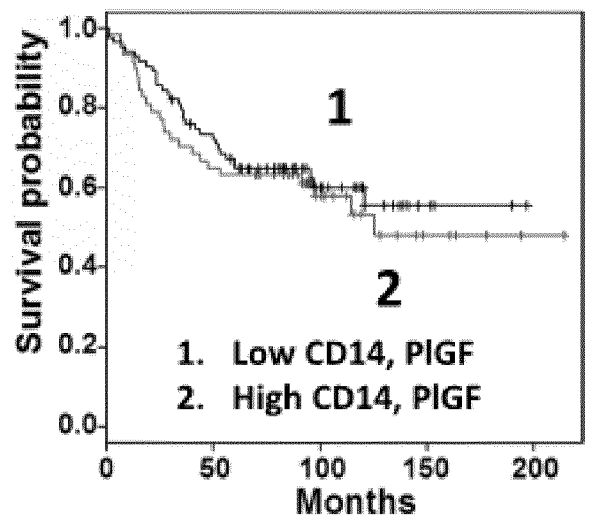

Fig. 5 A & B
A
| (n=120) | Fragments showing TIL growth (%) |
|---|---|
| + inhibitors | 72% |
| - inhibitors | 31% |
B
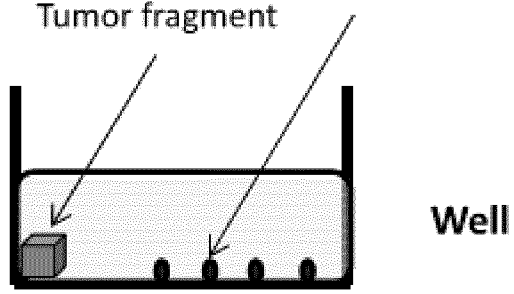
Well
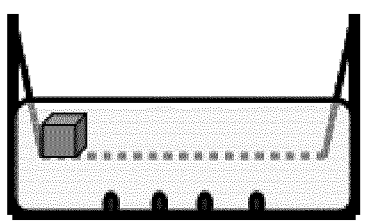
Transwell
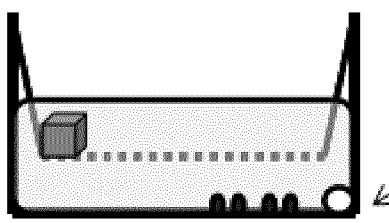
Transwell with chemokine gel

| Marker | Positivity in CD4 TIL | Positivity in CD8 TIL |
|---|---|---|
| EM CCR7-CD45RA- | 73% +/- 14% | 34% +/- 16% |
| CM CCR7+CD45RA- | 17% +/- 14% | 14% +/- 23% |
| TEMRA CCR7-CD45RA+ | 7.5% +/- 9% | 39% +/- 16% |
| NAÏVE CCR7+CD45RA+ | 2.2% +/- 1.6% | 13% +/- 10% |
| CD27 | 33% +/- 21% | 51% +/- 18% |
| CD28 | 43% +/- 20% | 11% +/- 13% |
| CD62L | 33% +/- 21% | 9% +/- 11.5% |
| PD1 | 56% +/- 32% | 33% +/- 10% |
| LAG-3 | 23.5% +/- 7% | 69% +/- 14% |
| TIM-3 | 61% +/- 12% | 68% +/- 9% |
| BTLA | 32% +/- 13% | 17% +/- 6% |
| CTLA-4 | 0.05% +/- 0.09% | 0.42% +/- 0.9% |
| 4-1BB (CD137) | 9% +/- 8% | 12% +/- 15% |

| Marker | Positivity in CD4 TIL | Positivity in CD8 TIL |
|---|---|---|
| EM CCR7-CD45RA- | 62% +/- 6% | 47.5% +/- 25% |
| CM CCR7+CD45RA- | 21% +/- 10% | 8.5% +/- 7% |
| TEMRA CCR7-CD45RA+ | 12.5% +/- 9% | 36% +/- 26% |
| NAÏVE CCR7+CD45RA+ | 4% +/- 3% | 8% +/- 5% |
| CD27 | 5% +/- 5% | 8% +/- 11% |
| CD28 | 62.5% +/- 17% | 17% +/- 15% |
| CD62L | 16% +/- 13% | 22% +/- 16% |
| PD1 | 9% +/- 6% | 8% +/- 7% |
| LAG-3 | 50% +/- 19% | 39% +/- 23% |
| TIM-3 | 50.5% +/- 20% | 57% +/- 22% |
| BTLA | 78.5% +/- 14.5% | 24% +/- 15% |
| CTLA-4 | 0.4% +/- 0.6% | 0.1% +/- 0.2% |
| 4-1BB (CD137) | 3% +/- 1% | 6% +/- 4% |

Fig. 6 B & C
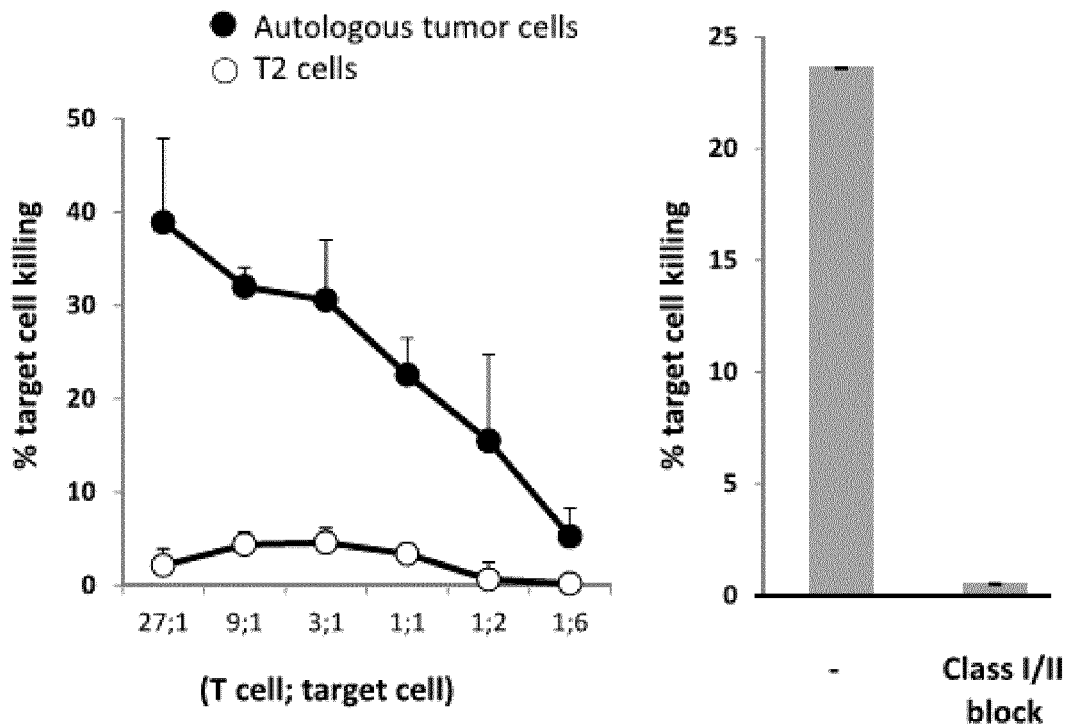
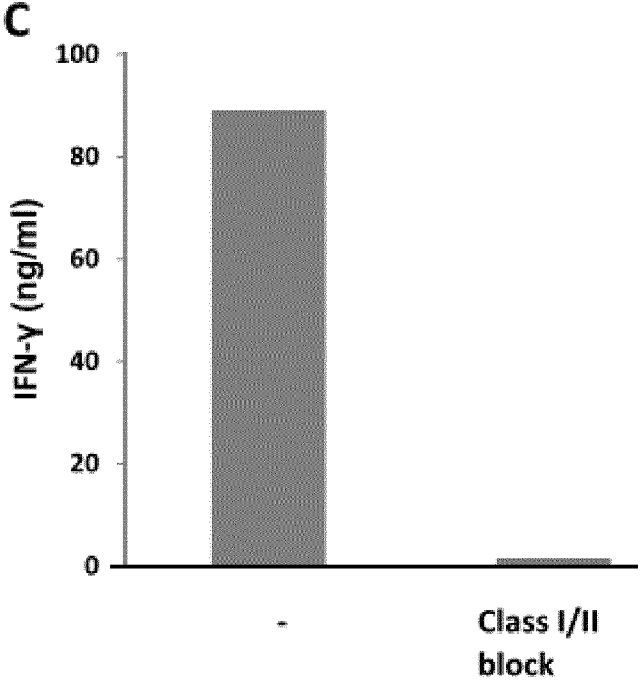

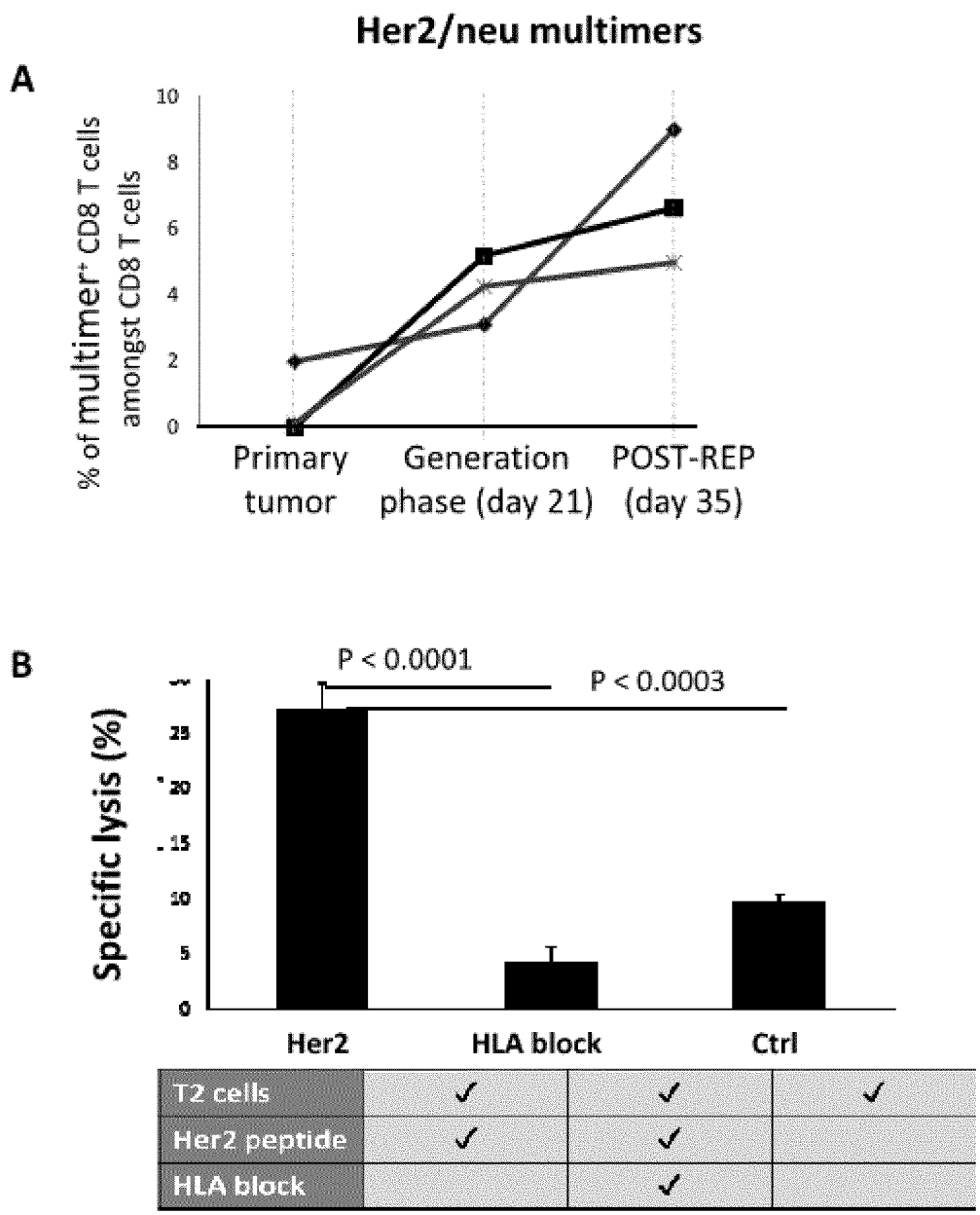
Fig. 8 A & B

ADOPTIVE IMMUNOTHERAPY FOR TREATING CANCER

PRIORITY STATEMENT

This application is a national stage application under 35 U.S.C. § 371 of PCT International Application No. PCT/EP2015/079867, which has an International filing date of 15 Dec. 2015 and claims priority to European Patent Application No. 14198399.9 filed on 17 Dec. 2014. The contents of each application recited above are incorporated herein by reference in their entirety.

FIELD OF THE INVENTION

The present invention provides methods for producing and/or expanding tumor-infiltrating lymphocytes (TILs) that can be used in adoptive immunotherapy in cancer treatment.

BACKGROUND OF THE INVENTION

Adoptive T-cell therapy (ACT) is a potent and flexible cancer treatment modality that can induce complete, durable regression of certain human malignancies such as melanoma (Dudley M E et al., 2003). Tumor-infiltrating lymphocytes (TILs) transfer proved to be the most effective therapy for metastatic melanoma reported so far, consisting of the generation of autologous T cells ex-vivo from tumor biopsies in the presence of high doses of IL-2, followed by the selection of TILs with best anti-tumor response (mainly based on IFN-γ secretion), their expansion (up to $10^{10}$-$10^{11}$ TILs) and re-infusion in patient (Dudley M E et al., 2003). Given the promising results of ACT in metastatic melanoma, TIL therapy is being tested nowadays for other types of cancers with less success, however.

The tumor microenvironment (TME) is heterogeneous, comprised of immune cells, soluble factors, extracellular matrix components, and mechanical and metabolic cues interacting with each other in a complex manner to suppress the anti-tumor immune response and to promote immune tolerance, tumor growth and metastasis. The mechanisms of tolerance and immune suppression are so diverse and robust in the TME that they may prevent the expansion of TILs. Thus, interventions aimed at overcoming these mechanisms may promote TIL expansion.

For these reasons, there is still a need to provide a reliable and efficient method for inducing robust expansion of functional tumor-specific TILs ex vivo from human cancer tissue for use in adoptive immunotherapy in cancer treatment.

BRIEF DESCRIPTION OF THE FIGURES

FIG. 1: Phenotypical and functional signature of pro-angiogenic TIE-2 Expressing Monocytes (TEM). A) TEM pro-angiogenic activity as measured by in vivo corneal vascularization assay. The pro-angiogenic activity of TEM isolated from peripheral blood and tumor of breast cancer patients was quantified by measuring the aptitude of TEM to induce cornea and iris vascularization. B) Secretion profile of cytokines and angiogenic factors in TEM isolated from patient blood and tumor and TEM differentiated in vitro. Angiogenic factors are boxed. C) Expression of TIE-2 and VEGFR-1 in blood and tumor TEM measured by flow cytometry. Shown are cumulated data of 5 experiments, significant variations (P<0.05) are indicated with an asterisk.

FIG. 2: Controlling the pro-angiogenic activity of TEM from breast cancer patients. A) In vivo corneal vascularization assay, as described in FIG. 1A, showing the variations in the pro-angiogenic activity of patient TEM in response to in silico predicted treatments. TIE-2 kinase inhibitor/TGF-β/VEGF treatment decreased tumor TEM pro-angiogenic activity while TNF-α/PlGF/ANG-2 treatment increased the pro-angiogenic activity of blood TEM. B) Variation of tumor TEM pro-angiogenic activity in response to TIE-2 or VEGFR kinase inhibitor treatments when alone or combined. C) Variations of patient blood and tumor TEM secretion profiles in response to TNF-α/PLGF/ANG-2 and TIE-2 kinase inhibitor/TGF-β/VEGF treatments. Significant variations (P<0.05) are indicated with an asterisk and angiogenic factors are boxed. No significant variations were detected for IL-4 and TNF-α. D) Variations of patient blood and tumor TEM expression of TIE-2 and VEGFR-1 in response to TNF-α/PLGF/ANG-2 and TIE-2 kinase inhibitor/TGF-β/VEGF treatments. Shown are cumulated data of 3 to 5 experiments.

FIG. 5: Expansion of TIL from breast tumor tissue fragments. A) Of 120 individual breast tumor fragments (from 10 distinct tumors) treated with TIE-2 and VEGFR kinase inhibitors, 72% show robust TIL expansion while only 31% of the fragments show TIL expansion in the absence of treatment. B) TIL culture formats: 24 well tissue culture plates were used made of regular well (top panel), transwell (middle panel) and transwell with a chemokine-containing gel in the lower compartment. C) Phenotype of TILs after 21 days of expansion in a regular well culture format.

FIG. 6: Phenotype and functions of TILs post-REP. A) Phenotype. B) Killing aptitude of TEM measured by chromium release assay using tumor cells derived from the primary tumor or T2 cells as specific and unspecific targets, respectively. The killing assay was performed in the presence or absence of MHC class I and class II blocking antibodies. TIL to tumor cell ratio was (9:1). C) Measure of IFN-γ release in the conditioned medium after 12 hours of TIL and tumor cell co-culture.

SUMMARY OF THE INVENTION

Figure 3:
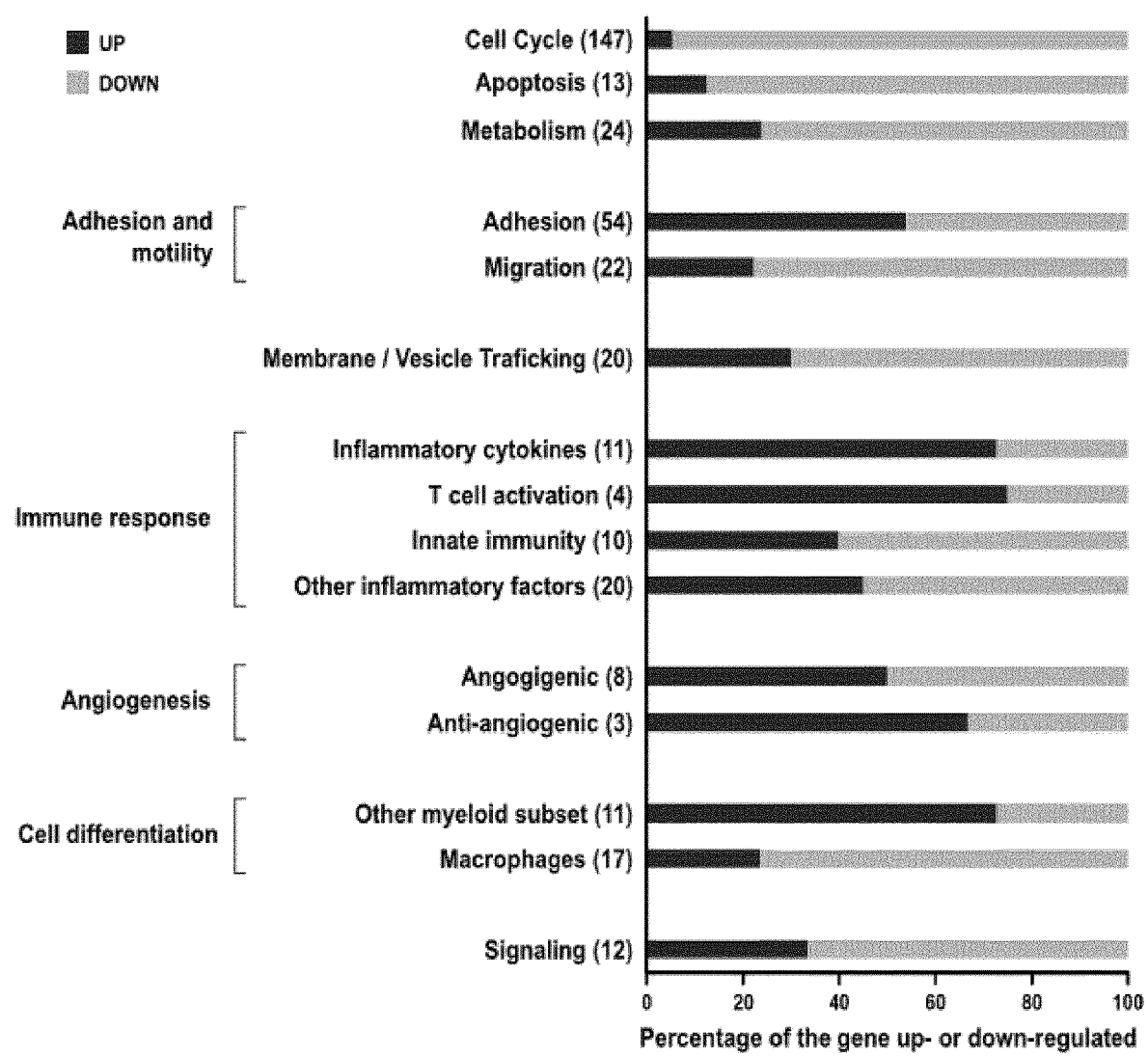
FIG. 3: Anti-angiogenic treatments reverse TEM into immunological potent monocytes. A) Gene expression changes in TEM in response to treatment reducing their pro-angiogenic activity. 398 significantly (P≤0.05) differentially expressed genes were manually annotated and classified in categories. In each category the percentage of up- and down-regulated genes are display as well as the total number of genes (under brackets). 50 genes could not be assigned to these categories. B) Survival analysis. The good prognostic effect of the lower expression of CD14, ANG-2 and PlGF (top panel) is reflected by the clear separation from the over expression group on the Kaplan-Meier plot, with a P value of 0.0257 from a Log-rank test, whereas only ANG-2 (middle panel) or PlGF (lower panel) combined with CD14 does not separate as well lower and over expression groups, suggesting a synergistic effect of ANG-2 and PlGF to promote CD14-mediated angiogenesis and the corresponding impact on patient relapse free survival.

The present invention provides a method for producing and/or expanding tumor-infiltrating lymphocytes (TILs) ex-vivo that can be used in adoptive immunotherapy in a patient in need of cancer treatment, said method comprising the steps of
i) obtaining one or more tumor fragments from the patient in need of cancer treatment,
ii) contacting said one or more tumor fragments with TIE-2 and VEGFR kinase inhibitor(s),
iii) culturing said one or more tumor fragments in the presence of one or more growth promoting substances, iv) expanding said TILs, and v) recovering the expanded TILs.

The present invention also concerns the use of TIE-2 and VEGFR kinase inhibitor(s) for the treatment of cancer in a patient in need thereof, including the steps of:
i) producing and/or expanding tumor-infiltrating lymphocytes (TILs) in accordance with the method of the invention so that the tumor-infiltrating lymphocytes proliferate and expand, and ii) administering said cultured and expanded tumor-infiltrating lymphocytes to the patient in need thereof.

Also provided is a method of treatment of cancer in a patient in need thereof comprising the steps of i) obtaining one or more tumor fragments, ii) contacting said one or more tumor fragments with TIE-2 and VEGFR kinase inhibitor(s), iii) culturing said one or more tumor fragments in the presence of one or more growth promoting substances, iv) expanding said TILs, v) recovering the expanded TILs, and vi) administering said recovered expanded TILs to the patient in need thereof.

Further provided is a pharmaceutical composition comprising a therapeutically effective amount of TIE-2 and VEGFR kinase inhibitor(s), pharmaceutically acceptable salts, solvates or esters thereof, for the treatment of cancer in a patient in need thereof.

Further provided is a pharmaceutical composition comprising a therapeutically effective number of TILs obtained in accordance with the methods of the invention for the treatment of cancer in a patient in need thereof.

Further provided is a kit for producing and/or expanding tumor-infiltrating lymphocytes (TILs) ex-vivo, comprising reagents, buffers, vials, and optionally instructions for use.

Further provided is a kit comprising i) a pharmaceutical composition comprising a therapeutically effective number of TILs obtained in accordance with the methods of the invention, or a ii) a pharmaceutical composition comprising a therapeutically effective amount of TIE-2 and VEGFR kinase inhibitor(s), pharmaceutically acceptable salts, solvates or esters thereof,
for the treatment of cancer in a patient in need thereof, and optionally instructions for use.

DESCRIPTION OF THE INVENTION

The present invention relates to a method for producing and/or expanding tumor-infiltrating lymphocytes (TILs) ex-vivo that can be used in adoptive immunotherapy in a patient in need of cancer treatment, said method comprising the steps of
i) obtaining one or more tumor fragments from the patient in need of cancer treatment,
ii) contacting said one or more tumor fragments with TIE-2 and VEGFR kinase inhibitor(s),
iii) culturing said one or more tumor fragments in the presence of one or more growth promoting substances, iv) expanding said TILs, and v) recovering the expanded TILs.

The term "comprise" is generally used in the sense of include, that is to say permitting the presence of one or more features or components. Alternatively, the term "comprise" or "comprising" also embraces the term "consist" or "consisting", respectively.

As used in the specification and claims, the singular form "a", "an" and "the" include plural references unless the context clearly dictates otherwise.

As used herein the term "patient" is well-recognized in the art, and refers to a mammal, including dog, cat, rat, mouse, monkey, cow, horse, goat, sheep, pig, camel, and, most preferably, a human.

Usually, the patient is a patient in need of cancer treatment. The term "patient" does not denote a particular age or sex. Thus, adult, infant and newborn subjects, whether male or female, are intended to be covered.

As used herein, "adoptive immunotherapy" is a process whereby in vitro or ex vivo expanded lymphoid cells are transferred, administered or introduced into an individual or host. When the lymphoid cells are cultured in vitro under appropriate conditions certain subpopulations thereof are selectively expanded. The expanded subpopulations of cells that are produced are herein referred to as in vitro expanded lymphoid cells. The subpopulation of cells is generally a heterogeneous mixture of cells having different phenotypes, but it may also consist of a homogeneous population of cells. The particular mixture of cells that are produced is a function of the starting material and the conditions under which such cells are generated. If the lymphoid cells that are expanded in the presence of a cytokine are derived from a tumor, then the in vitro expanded lymphoid subpopulation of cells that is produced are referred to as tumor-infiltrating lymphocytes (TILs) which are a type of white blood cell found in tumors that are implicated in killing tumor cells.

As used herein, a "growth promoting substance" is a substance that in some manner participates in or induces cells to grow and/or divide. Examples of growth promoting substances include mitogens and cytokines.

A mitogen, as used herein, is a substance that induces cells to divide and in particular in the present invention, is a substance that stimulate a lymphocyte population in an antigen-independent manner to proliferate and differentiate into functional TILs. Examples of such substances include lectins, lipopolysaccharides and toll-like receptor agonists.

Examples of cytokine are selected from the group comprising a chemokine, an interleukin, an interferon (such as IFN-α or IFN-δ) and any other of such factors that are known to those of skill in the art.

In case the cytokine is an interleukin, then said interleukin is preferably selected from the group comprising interleukin-2, interleukin-4, interleukin-6, interleukin-7, interleukin-12, interleukin-15, interleukin-21 and a functionally similar interleukin, or a combination of one or more of these interleukins. Most preferably, the interleukin is selected from the group comprising IL-2, IL-7 and IL-15, or a combination of two or more of these interleukins (e.g. IL-2/IL-7; IL-2/IL-15; IL-7/IL-15; or IL-2/IL-7/IL-15).

By the term "functionally similar interleukin" is meant that the effect observed are comparable to the effect observed by the cytokines mentioned in the context of the present invention. These functionally similar compounds may substitute the specifically mentioned compounds in the specific process referred to. Examples of functionally similar interleukins are interleukin derivatives, or mutants, of IL-2, IL-7 and IL-15 that can improve T cell proliferation, T cell survival or T cell effector functions.

In case the cytokine is a chemokine, then said chemokine is preferably selected from the group comprising a CXC chemokine family. Most preferably, the chemokine is selected from the group comprising CXCL-9 and/or CXCL-10. Any other of such chemokine that are known to those of skill in the art, in particular any ligand for the receptor CXCR3, are also envisioned.

In accordance with the method described herein, one or more tumor fragments are obtained from the patient in need of a cancer treatment by adoptive immunotherapy. Usually, these one or more tumor fragments originated from a surgical piece comprising the tumor that was resected by surgery from the subject to be treated or that was obtained by any of a number of methods as are known in the art.

Usually, the one or more tumor fragments measuring about 1 to 3 mm, preferably 1.5 to 2 mm, most preferably about 1.5 mm, are cut with, for example, a scalpel from different areas of the tumor and are placed in culture as described in Dudley M E et al., 2003 or cryopreserved in FCS containing 10% DMSO, or any other viable cryopreserving media, for future use. Typically, the one or more tumor fragments has a size approximately comprised between 2 to 9 mm$^3$, preferably between 4 to 6 mm$^3$.

The one or more tumor fragments are then contacted with TIE-2 inhibitor and VEGFR kinase inhibitor or with (combined) TIE-2 and VEGFR kinase inhibitor, usually in culture medium, preferably during 2-20 hours, most preferably during 5 to 15 hours, more preferably during 7 to 15 hours, even more preferably during 10 to 12 hours. A typical culture medium consists in RPMI 1640 medium supplemented with about 10% Fetal Calf Serum or about 10% human serum or any other serum-free media for T cell expansion. Following exposure to the inhibitors, the fragments are washed 3 times for 5 min in RPMI1640 medium containing 10% FCS (or human serum), and each fragment is placed in a well of a 24 well tissue culture plate in 1.5 to 2 ml of RPMI1640 supplemented with 10% FCS (or 10% human serum) in the presence of 5000-8000 U/ml, preferably about 6000 U/ml of IL-2 (pre-REP phase).

According to the invention, the TIE-2 kinase inhibitor is usually selected from the group comprising compound 7 ((5-[4-[[[2-[[(1S)-1-Cyclohexylethyl]amino]-2-oxoethyl][(4methylphenoxy)carbonyl]amino]methyl]phenyl]-3-pyridinecarboxylic acid)), SB-203580 ((4-[5-(4-Fluorophenyl)-2-[4-(methylsulfonyl)phenyl]-1H-imidazol-4-yl]pyridine)), and 4-(6-Methoxy-2-naphthyl)-2-(4-methylsulfinylphenyl)-5-(4-pyridyl)-1H-imidazole, cabozantinib, Altiratinib, SB633825 (4-(5-(6-methoxynaphthalen-2-yl)-2-(4-(methylsulfinyl)phenyl)-1H-imidazol-4-yl)pyridine) or a combination of two or more of these TIE-2 kinase inhibitors.

The VEGFR kinase inhibitor is usually selected from the group comprising Vatalanib (PTK787), Tivozanib (AV-951), VEGFR Tyrosine Kinase Inhibitor V, (C25H22N2O4.HCl.H2O), VEGFR Tyrosine Kinase Inhibitor II (C19H16ClN3O), Sorafenib Tosylate, Sunitinib, Malate, Ponatinib, Axitinib, Foretinib, Vandetanib, Nintedanib, Regorafenib, Pazopanib, Cediranib, Dovitinib, Linifanib, Tivozanib, Motesanib Diphosphate, Lenvatinib, Pazopanib, KRN 633, and ZM 306416 or a combination of two or more of these VEGFR kinase inhibitors. Most preferably, the VEGFR kinase inhibitor is Vatalanib (PTK787).

Figure 7:
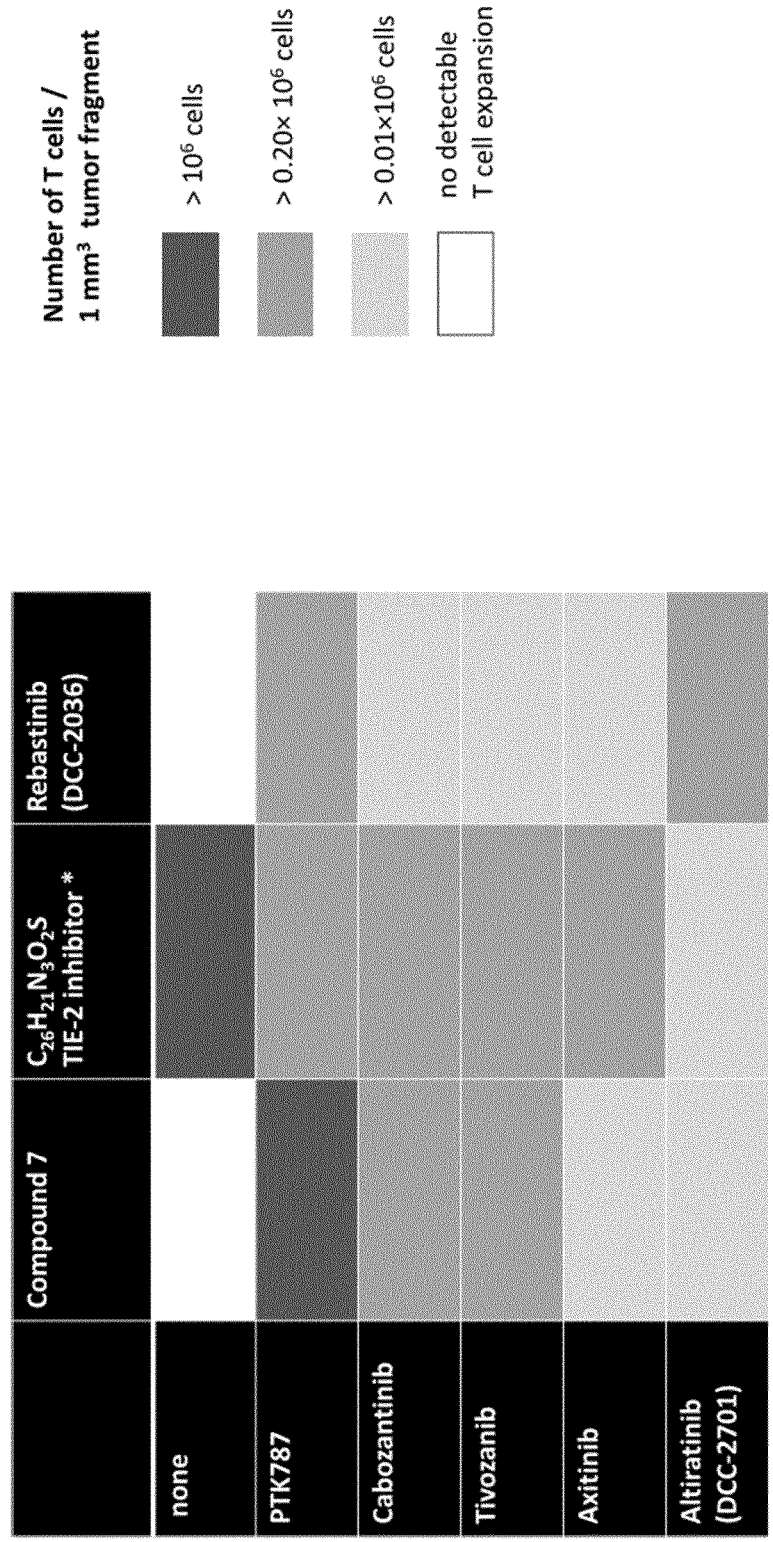
FIG. 7: Expansion of TIL in vitro from breast tumor fragments treated with various TIE-2 and VEGFR kinase inhibitors. The number of T cells obtained after 20 days in culture in the presence of high doses of IL-2 (generation phase) is indicated.

Referring in more details to the examples and in particular to FIG. 7, the one or more tumor fragments are preferably contacted with the following TIE-2 inhibitor and VEGFR kinase inhibitor: Compound 7 and PTK787; Compound 7 and cabozantinib; Compound 7 and Tivozanib; Compound 7 and Axitinib; Compound 7 and Altiratinib; SB633825 and PTK781; SB633825 and cabozantinib; SB633825 and Tivozanib; SB633825 and Axitinib; SB633825 and Altiratinib; Rebastinib and PTK787; Rebastinib and cabozantinib; Rebastinib and Tivozanib; Rebastinib and Axitinib; and Rebastinib and Altiratinib.

Alternatively, the invention also envisioned the use of one or more combined inhibitors that exhibit both TIE-2 and VEGFR kinase inhibitor activities. This combined TIE-2 and VEGFR kinase inhibitor is selected from the group comprising MGCD-265, Rebastinib (DCC-2036), 4-(5-(6-methoxynaphthalen-2-yl)-2-(4-(methylsulfinyl)phenyl)-1H-imidazol-4-yl)pyridine, SB633825 (4-(5-(6-methoxynaphthalen-2-yl)-2-(4-(methylsulfinyl)phenyl)-1H-imidazol-4-yl)pyridine), Altiratinib and Cabozantinib, or a combination of two or more of these inhibitors.

Alternatively also, a compound known as VEGFR kinase inhibitor can also exert, when used at a different dose or in different conditions, a TIE-2 kinase inhibitor activity (and vice versa). Examples of such compounds are selected from the group comprising MGCD-265, Rebastinib (DCC-2036), SB633825: 4-(5-(6-methoxynaphthalen-2-yl)-2-(4-(methylsulfinyl)phenyl)-1H-imidazol-4-yl)pyridine, SB633825 (4-(5-(6-methoxynaphthalen-2-yl)-2-(4-(methylsulfinyl)phenyl)-1H-imidazol-4-yl)pyridine), Altiratinib and Cabozantinib.

Throughout the specification (description and claims), it is understood that when the term inhibitor is used in its plural form, it refers to at least one TIE-2 inhibitor and to at least one VEGFR kinase inhibitor. However, when this term is used in its singular form, it relates to a combined TIE-2 and VEGFR kinase inhibitor. For the ease of reading, the term inhibitor is written with an "s" into brackets that means that it refers to, and encompasses, the two aspects of the invention discussed above.

Before culturing said one or more tumor fragments in the presence of one or more growth promoting substances, the one or more tumor fragments can be washed several times with culture medium, e.g. RPMI supplemented with 10% serum, or any other serum-free media for T cell expansion, for about 5 min at about 22° C.

Then, the one or more tumor fragments are cultured in presence of one or more growth promoting substances for a time sufficient to generate the TILs. Preferably, the growth promoting substance is selected from the group described above. Most preferably, the growth promoting substance is an interleukin selected from the group comprising IL-2, IL-7 and IL-15 or a combination of two or more of these interleukins e.g. IL-2/IL-7; IL-2/IL-15; IL-7/IL-15; or IL-2/IL-7/IL-15.

The one or more tumor fragments are cultured for a time sufficient to generate the TILs, i.e. between 14-28 days, preferably between 18-23 days, more preferably between 20-23 days, most preferably about 21 days in presence of one or more growth promoting substances.

The culture of the one or more tumor fragments is usually done in the presence of high doses of interleukins selected from the group comprising IL-2, IL-7 and IL-15 or a combination of two or more of these interleukins. Generally, IL-2 is added at a dose of 5000-8000 U/ml, preferably about 6000 U/ml, whereas IL-7 and IL-15 are added at a dose of about 5-20 ng/ml (each), most preferably at a dose of about 8-15 ng/ml (each), more preferably at a dose of about 10 ng/ml (each).

The generated TILs are then expanded during a time sufficient to obtain a therapeutically effective number of said TILs using one or multiple rounds of expansion, i.e. repeated several times (1×, 2×, 3×, etc. . . . ). Usually, a round of expansion is done in the presence of feeder cells such as, for example, irradiated allogenic PBMC, artificial or autologous antigen presenting cells (APC), or a combination of two or more of these feeder cells. Any expanding techniques known in the art, such as for example the protocol described in Dudley M E et al., 2003 can be used in the present invention.

Alternatively, the expansion of said TILs is performed in the presence of feeder cells and/or an anti-CD3 antibody, an anti-CD28 antibody, an anti-CD137 antibody or a recombinant ligand of CD137, or a combination of two or more of these antibodies or ligands.

The expansion of said TILs is usually performed by culturing said TILs during a time sufficient to obtain a therapeutically effective number of said cells which is between 7-35 days, preferably between 10-28 days, more preferably between 12-23 days, most preferably about 14-15 days.

The therapeutically effective number of TILs refers to the number of said cells that is at least sufficient to achieve a therapeutic effect when said TILs are used in adoptive immunotherapy. Generally, this therapeutically effective number is comprised between about $0.5 \times 10^9$ cells to about $300 \times 10^9$ cells, preferably between about $1 \times 10^9$ cells to about $250 \times 10^9$ cells, more preferably between about $10 \times 10^9$ cells to about $200 \times 10^9$ cells, most preferably about $20 \times 10^9$ cells to about $150 \times 10^9$ cells, even most preferably about $40 \times 10^9$ cells to about $100 \times 10^9$ cells, and about $50 \times 10^9$.

The expanded TILs are then recovered by any techniques known in the art, such as for example by concentration or centrifugation, optionally followed by one or more extensive washes. Alternatively or additionally, the tumor-specific TILs can also be recovered and enriched using any cell separation method allowing the selective isolation of tumor-specific TILs, preferably said methods are selected from the group comprising affinity-based cell capture.

All cultures described herein are usually done in culture medium at 37° C. in 5% $CO_2$.

As shown in the examples, the expanded and recovered TILs are CD4 and/or CD8 cells that, preferably display a memory phenotype. A fraction of them, preferably about 0.8%-2%, most preferably about 0.8-1.3%, display a stem cell (TSCM) phenotype ($CD45RA^+$, $CD95^+$, $CD62L^+$, $CCR7^+$, $IL2R$-$\beta^+$). $T_{SCM}$ is a long-lived memory T cell population that has been reported to show an enhanced capacity for self-renewal, a multipotent ability to derive central memory, effector memory and effector T cells and a superior aptitude to mediate anti-tumor response in a humanized mouse model (Gattitoni et al., Nature Medicine, 2011; Restifo and Gattitoni, Current opinion in immunology, 2013).

Preferably also, the expanded and recovered TILs are tumor-specific CD8 cells that express high levels of CD137, CD28 and BTLA on their membrane surface.

In another aspect, the method of the invention further comprises a selection and/or enriching procedure of the TILs before or after the expansion phase. Such selection and/or enriching procedure can for example be based on the tumor-specific TILs phenotype, i.e. on the receptors they express on their membrane surface. Preferably, said ligand is an antibody specific for a TIL cell surface receptor such as, e.g. an anti-CD137 antibody, an anti-CD28 antibody or an anti-BTLA antibody. Most preferably, said ligand is an anti CD137 antibody.

The method for producing and/or expanding tumor-infiltrating lymphocytes (TILs) described herein can be applied to the treatment of any kind of cancer, in particular to the treatment of one or more cancers selected from the group comprising melanoma, ovarian cancer, gastrointestinal cancer, glioma, head and neck carcinoma, cervix cancer, breast cancer, pancreatic cancer, and lung cancer. Most preferably, the cancer is selected from the group comprising breast cancer and ovarian cancer. Even more preferably, the cancer is breast cancer.

The present invention also relates to a composition comprising TILs produced, expanded and recovered in accordance with the methods of the invention for use in the treatment of cancer in a patient in need thereof.

The expanded and recovered TILs obtained with the methods of the invention are CD4 and/or CD8 cells that, preferably display a memory phenotype. A fraction of them, preferably 0.8%, most preferably, 1.3% display a stem cell ($T_{SCM}$) phenotype. Preferably also, the expanded and recovered TILs are tumor-specific CD8 cells that express high levels of CD137, CD28 and BTLA on their membrane surface.

Also envisioned is a pharmaceutical composition comprising a therapeutically effective amount of TIE-2 and VEGFR kinase inhibitor(s), pharmaceutically acceptable salts, solvates or esters thereof, for the treatment of cancer in a patient in need thereof.

Usually also the pharmaceutical composition of the invention further comprises a pharmaceutically acceptable excipient. In some aspects, it may also contain one or more additional active ingredients.

The content of TIE-2 and VEGFR kinase inhibitor(s) in the pharmaceutical composition of the present invention varies depending on the subject of administration, route of administration and target cancer, among other variables.

The term "therapeutically effective", in the present invention, refers to the amount of TIE-2 and VEGFR kinase inhibitor(s) used is of sufficient quantity to ameliorate one or more symptoms of cancer. Such amelioration only requires a reduction or alteration, not necessarily elimination.

The pharmaceutical composition of the present invention may be administered orally, topically (e.g., transdermal, etc.), vaginally, rectally, or parenterally (e.g., subcutaneous, intramuscular, intrasternal, intratumoral or intravenous injection). Preferably, the pharmaceutical composition is administered parenterally, most preferably by subcutaneous, intravenous or intratumoral injection. Alternatively, the pharmaceutical composition of the invention may be administered, prior to, during and/or after the patient was subjected to an additional anticancer treatment such as, e.g. surgery, chemotherapy, radiation therapy, hormonal therapy, and targeted therapy (including immunotherapy such as monoclonal antibody therapy).

Examples of topical administration of the pharmaceutical composition include transdermal, buccal or sublingual application. For topical applications, the pharmaceutical composition can be suitably admixed in a pharmacologically inert topical carrier, such as a gel, an ointment, a lotion or a cream. Such pharmacologically inert topical carriers include water, glycerol, alcohol, propylene glycol, fatty alcohols, triglycerides, fatty acid esters, or mineral oils. Other possible pharmacologically inert topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added.

For oral administration, the pharmaceutical composition may be administered as a capsule, tablet or granule. Tablets may contain various excipients such as microcrystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinylpyrrolidone, sucrose, gelatin and acacia. In a certain aspect, the tablet may be film coated. Additionally, lubricating agents such as magnesium stearate, sodium lauryl sulfate and talc are often very useful for tablets. Other solid compositions may also be employed as fillers in gelatin capsules; preferred materials in this connection also include lactose or milk sugar as well as high molecular weight polyethylene glycols. When aqueous suspensions and/or elixirs are desired for oral administration, the TIE-2 and VEGFR kinase inhibitor(s) may be combined with various sweetening or flavoring agents, coloring matter or dyes, and, if so desired, emulsifying and/or suspending agents, together with such diluents as water, ethanol, propylene glycol, glycerin and various like combinations thereof. The pharmaceutical composition may be formulated such that the TIE-2 and VEGFR kinase inhibitors are released over a period of time after administration.

The pharmaceutical composition comprising the TIE-2 and VEGFR kinase inhibitor(s) along with a pharmaceutically acceptable excipient and, optionally, an additional active ingredient, may be prepared by any conventional technique known in the art.

Generally, the amount of TIE-2 and VEGFR kinase inhibitor(s) present in the pharmaceutical composition is about 0.01% to about 90% by weight relative to the whole composition. A suitable therapeutically effective amount of the TIE-2 and VEGFR kinase inhibitors will typically range from about 0.01 mg/kg to about 1 g/kg of body weight per day; from about 1 mg/kg to about 600 mg/kg body weight per day; from about 1 mg/kg to about 250 mg/kg body weight per day; from about 10 mg/kg to about 400 mg/kg body weight per day; from about 10 mg/kg to about 200 mg/kg of body weight per day; from about 10 mg/kg to about 100 mg/kg of body weight per day; from about 10 mg/kg to about 25 mg/kg body weight per day; from about 1 mg/kg to about 10 mg/kg body weight per day; from about 0.001 mg/kg to about 100 mg/kg of body weight per day; from about 0.001 mg/kg to about 10 mg/kg of body weight per day; from about 0.001 mg/kg to about 1 mg/kg of body weight per day.

The desired dose may be administered once daily, or by several sub-divided doses, e.g., 2 to 5 sub-divided doses, at appropriate intervals through the day, or other appropriate schedule.

The term "pharmaceutically acceptable excipient" as used herein includes, but is not limited to, one of more of the following: polymers, resins, plasticizers, fillers, lubricants, diluents, binders, disintegrants, solvents, co-solvents, surfactants, buffer systems, preservatives, sweetener agents, flavoring agents, pharmaceutical-grade dyes or pigments, chelating agents, viscosity agents, and combinations thereof. Pharmaceutically acceptable excipients can be used in any component in making the dosage form, i.e. core tablet or coating. Flavoring agents and dyes and pigments among those useful herein include but are not limited to those described in Handbook of Pharmaceutical Excipients (4th Ed., Pharmaceutical Press 2003). Suitable co-solvents include, but are not limited to, ethanol, isopropanol, acetone, and combinations thereof. Suitable surfactants include, but are not limited to, polyoxyethylene sorbitan fatty acid esters, polyoxyethylene monoalkyl ethers, sucrose monoesters, simethicone emulsion, sodium lauryl sulfate, Tween 80®, and lanolin esters, ethers, and combinations thereof. Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, propyl paraben, and combinations thereof. Suitable fillers include, but are not limited to, starch, lactose, sucrose, maltodextrin, and microcrystalline cellulose. Suitable plasticizers include, but are not limited to, triethyl citrate, polyethylene glycol, propylene glycol, dibutyl phthalate, castor oil, acetylated monoglycerides, triacetin, and combinations thereof. Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, Eudragit® F530D and Eudragit® S 100 (Rohm Pharma GmbH and Co. KG, Darmstadt, Germany), Acryl-EZE® and Sureteric® (Colorcon, Inc., West Point, Pa.), and combinations thereof. Suitable lubricants include, but are not limited to, magnesium stearate, stearic acid, talc, and combinations thereof.

The term "additional active ingredient" as used herein includes any agent known in the art to treat, prevent or reduce the symptoms of the cancer being treated by the pharmaceutical composition.

The present invention also envisioned a pharmaceutical composition comprising a therapeutically effective number of TILs obtained in accordance with the methods described herein for the treatment of cancer in a patient in need thereof. The pharmaceutical composition of the invention can further comprise a pharmaceutically acceptable excipient.

The expanded and recovered TILs obtained with the methods of the invention are CD4 and/or CD8 cells that, preferably display a memory phenotype. A fraction of them, preferably 0.8%, most preferably, 1.3% display a stem cell ($T_{SCM}$) phenotype. Preferably also, the expanded and recovered TILs are tumor-specific CD8 cells that express high levels of CD137, CD28 and BTLA on their membrane surface.

Additionally, the pharmaceutical composition further comprises a therapeutically effective amount of a cytokine selected from the group comprising a chemokine, an interleukin and an interferon (IFN-α or IFN-δ) or a combination of two or more of these cytokines.

In case the cytokine is an interleukin, then said interleukin is preferably selected from the group comprising interleukin-2, interleukin-4, interleukin-6, interleukin-7, interleukin-12, interleukin-15, interleukin-21 and a functionally similar interleukin, or a combination of one or more of these interleukins. Most preferably, the interleukin is selected from the group comprising IL-2, IL-7 and IL-15, or a combination of two or more of these interleukins (e.g. IL-2/IL-7; IL-2/IL-15; IL-7/IL-15; or IL-2/IL-7/IL-15).

The pharmaceutical composition comprising a therapeutically effective number of TILs may be administered topically (e.g., transdermal, etc.) or parenterally (e.g., subcutaneous, intramuscular, intrasternal, intratumoral or intravenous injection). Preferably, the pharmaceutical composition is administered parenterally, most preferably by subcutaneous, intravenous or intratumoral injection.

The pharmaceutical composition comprising a therapeutically effective number of TILs may be administered, prior to, during and/or after the patient was subjected to an additional anticancer treatment such as, e.g. surgery, chemotherapy, radiation therapy, hormonal therapy, and targeted therapy (including immunotherapy such as monoclonal antibody therapy). Preferably, the pharmaceutical composition is administered after the patient was subjected to chemotherapy, most preferably after depletive chemotherapy.

As described supra, the therapeutically effective number of TILs refers to the number of said cells that is at least sufficient to achieve a therapeutic effect when said TILs are used in adoptive immunotherapy. Generally, this therapeutically effective number is comprised between about $0.5 \times 10^9$ cells to about $300 \times 10^9$ cells, preferably between about $1 \times 10^9$ cells to about $250 \times 10^9$ cells, more preferably between about $10 \times 10^9$ cells to about $200 \times 10^9$ cells, most preferably about $20 \times 10^9$ cells to about $150 \times 10^9$ cells, even most preferably about $40 \times 10^9$ cells to about $100 \times 10^9$ cells, and about $50 \times 10^9$.

The present invention also relates to a method of treatment of cancer in a patient in need thereof comprising the steps of i) obtaining one or more tumor fragments, ii) contacting said one or more tumor fragments with TIE-2 and VEGFR kinase inhibitor(s), iii) culturing said one or more tumor fragments in the presence of one or more growth promoting substances, iv) expanding said TILs to obtain a therapeutically effective number of said TILs, v) recovering the expanded TILs, and vi) administering said recovered expanded TILs to the patient in need thereof.

As used herein, the term "treatment" refers to the medical management of a patient with the intent to cure, ameliorate, stabilize, a cancer. This term includes active treatment, that is, treatment directed specifically toward the improvement of said cancer and condition associated with cancer and also includes causal treatment, that is, treatment directed toward removal of the cause of the condition associated with cancer.

This method of treatment of cancer can further comprise a step vii) of administering a pharmaceutically effective amount of both TIE-2 kinase inhibitor and VEGFR kinase inhibitor(s) to the patient in need thereof prior, after or concomitant to the administration of the cultured and expanded tumor-infiltrating lymphocytes.

Alternatively, the method of treatment of cancer described above further comprises administering an additional anticancer treatment selected from the group comprising chemotherapy, radiotherapy, targeted therapy (including immunotherapy such as monoclonal antibody therapy), hormone therapy and a cytokine.

Examples of cytokine are selected from the group comprising a chemokine, an interleukin, an interferon (such as IFN-α or IFN-δ) and any other of such factors that are known to those of skill in the art. Most preferably, the cytokine is administered intravenously, subcutaneously or intratumorally.

In case the cytokine is an interleukin, then said interleukin is preferably selected from the group comprising interleukin-2, interleukin-4, interleukin-6, interleukin-7, interleukin-12, interleukin-15, and interleukin-21, a functionally similar interleukin, or a combination of one or more of these interleukins. Most preferably, the interleukin is selected from the group comprising IL-2, IL-7 and IL-15, or a combination of two or more of these interleukins (e.g. IL-2/IL-7; IL-2/IL-15; IL-7/IL-15; or IL-2/IL-7/IL-15). Even more preferably, the interleukin is IL-2 or a combination of IL-7/IL-15.

Also encompassed in the present invention is a kit for producing and/or expanding tumor-infiltrating lymphocytes (TILs) ex-vivo, comprising reagents, buffers, vials, and optionally instructions for use. These reagents may for example be selected from the group comprising one or more growth promoting substances.

The kit may also comprise all the necessary material, such as microcentrifuge tubes, necessary to practice the methods of the invention.

Also encompassed in the present invention is a kit comprising either i) a pharmaceutical composition comprising a therapeutically effective number of TILs obtained in accordance with the methods described herein or a ii) a pharmaceutical composition comprising a therapeutically effective amount of TIE-2 and VEGFR kinase inhibitor(s), pharmaceutically acceptable salts, solvates or esters thereof, for the treatment of cancer in a patient in need thereof, and optionally instructions for use.

EXAMPLES

Example 1

Material and Methods
Tissue Specimens, Processing and Cryopreservation of Tumor Tissue Fragments This study was approved by the ethics committee of the University Hospital of Lausanne. Patient tissue specimens were obtained according to the declaration of Helsinki and upon written informed consent. Patient peripheral blood was collected before surgery and PBMC isolated by Ficoll-Hypaque density gradient. A series of 40 primary invasive breast carcinoma specimens (Table 2) were resected from patients with breast cancer. All patients underwent surgery and sentinel node biopsy and were untreated before surgery. The presence of nodal metastases and tumor pathological features were confirmed histologically and are detailed in Table 2. Fragments of tumor measuring about 1.5 mm in each dimension were cut with a scalpel from different areas of the tumor specimen and places in culture as previously described or cryopreserved in FCS containing 10% DMSO. Buffy coats were obtained from the local blood bank and allogenic irradiated PBMC (Peripheral Blood Mononuclear Cells) were prepared as previously described (Dudley et al., 2003) following Ficoll-Hypaque gradient centrifugation.

TABLE 2

Clinical and pathological features of tumors and patients (n = 40)

| Patient characteristics | % |
|---|---|
| Age, years | |
| <50 | 29.6 |
| ≥50 | 70.4 |
| Surgical treatment | |
| Mastectomy | 32.1 |
| Tumorectomy | 67.9 |
| Lymph node status | |
| Negative | 74.5 |
| Positive | 25.5 |
| Tumor | |
| T1 | 57.1 |
| T2 <3 cm | 42.9 |
| Histology | |
| Ductal | 84.7 |
| Lobular | 11.5 |
| Others | 3.8 |
| Grade | |
| I | 30.8 |
| II | 38.4 |
| III | 30.8 |

Reagents and Antibodies

Reagents unless indicated otherwise were purchased from Sigma Aldrich. TIE-2 kinase inhibitor compound 7 was from Alexis Chemicals or Santa Cruz Biotechnologies. PTK787 (vatalanib) was from Selleckchem. Matrigel was from Beckton Dikinson, Recombinant human CXCL-9 and CXCL-10 were from Raybiotech, recombinant human IL-7 and IL-15 were from Miltenyi, recombinant human IL-2 was a gift from GlaxoSmithKline._Plastic 24 well plate and transwell tissue culture plates (pore size: 8 µm) were from Corning and plastic tissue culture flask were from TPP. Fetal Calf Serum (FCS) and RPMI 1640 medium were from life technologies. Human serum was prepared in the laboratory from peripheral blood of male AB healthy donors obtained from the blood bank of Bern.

TEM Isolation and Stimulation

Monocytes were isolated from patient specimen (peripheral blood or tumor) using CD14 immunomagnetic selection (StemCell Technologies Inc.). Immunomagnetically isolated cells were stimulated as described above, extensively washed and used for functional assays. Monocytes were resuspended in PRMI1640 medium containing 2% FCS at a concentration of 1 million/ml for 2 h at 37° C. The cells were exposed to the different ligand/TIE-2 kinase inhibitor (at a final concentration of 10 µM) combinations for 2 h at 37° C. All recombinants ligands were used at 100 ng/ml but TNF-α (20 ng/ml). The cells were washed and cultured for 36 h in RPMI containing 10% FCS. At the end of the stimulation, the cells were extensively washed and kept in RPMI1640 containing 10% FCS. TEM phenotype and cytokine profile were assessed by flow cytometry using of cells and conditioned medium, respectively.

Analysis of TIL Phenotype and Functions

Following blocking of Fc receptors with antibodies, cells were labeled with CD27 FITC Biolegend (M-T271), CD137 PerCp Cy5.5 BioLegend, CD62L PE Biolegend (DREG-56), CD45RA PE-ECD Beckman Coulter, CD4 PE Cy7 Biolegend (SK3), CD8 APC Biolegend, CD28 A700 BioLegend (CD28.2), CD3 APC Cy7 BioLegend (UCHT1), CCR7 BV421 BD (150503), PD1 BV650 eBioscience, CD95 BV705 BD (DX2), CD14 PerCP-Cy5.5 BD, CD11b FITC BD, TIE-2 Alexa 647 BioLegend), VEGFR-1 PE (RnD) and analysed by flow cytometry using a Facs LSRII (BD Biosciences). T cell killing aptitude was assessed by chromium release assay (Rosato, 1999). Secreted cytokines and were quantified in cell co-culture conditioned medium using FlowCytomix technology (eBioscience and RnD).

In Vivo and In Vitro Angiogenesis Assay

Mouse experiments were approved by the veterinary service of Vaud Canton. The bacterial lipopolysaccharide membrane receptor CD14 is a component of the innate immune system mainly expressed by monocytes and macrophages and commonly used as a marker of these cell populations. Monocytes were isolated by CD14 immunomagnetic selection from patient tissue. For in vivo corneal vascularization assay, 20,000 CD14$^+$ cells isolated by positive immunomagnetic selection (Stemcell Technologies) from peripheral blood (purity>95%) or dissociated tumors (purity>85% with no detectable CD45$^-$ contamination) were injected (5 µl) into the stromal part of the corneas of anesthesized NOD-scid IL2Rγ$^{null}$ mice using a 35 gauge nanofil injection kit (WPI, Stevenage, UK). Cornea vascularization was monitored with a digital stereomicroscope (Leica). Mice were euthanized 25 days post-injection and isolated eyes were fixed in 4% PFA, cryoprotected in a 30% sucrose solution and embedded in Yazulla media (30% egg albumin, 3% gelatin). Vascularization was assessed by immunostaining of the sagittal sections (10 m) with CD31-specific antibodies (Platelet Endothelial Cell Adhesion Molecule-1, PECAM-1) using a Zeiss motorized Axio Imager M1 fluorescent microscope. In vitro angiogenesis sprouting assay was performed with HUVEC spheroids as previously described (Korff Tetal., 1999). The corneal angiogenesis assay is still considered one of the best in vivo assays (Auerbach R et al., 2003). However, the surgical procedure is technically difficult and the assay time consuming. Therefore, we use in vitro angiogenesis sprouting assay (Korff Tetal., 1999) to assess the impact of multiple treatments and we validated the most relevant one in vivo.

Expansion of TILs and Tumor Cells from Primary Breast Tumors

Following sectioning of the tumor tissue into small fragments (1.5 mm in each dimension), the dissociated cells which leak out the tumor fragments were centrifuged and tumor cells expanded according to a recently established protocol (Palechor-Ceron N er al., 2013) while TILs were expanded from breast tumor tissue fragments as described (Dudley et al., 2003).

Gene Expression Profiling

Total RNAs from 100 000 monocytes were isolated and purified with the Qiagen RNeasy micro plus kit. RNA samples were hybridized to Affymetrix Human Gene 1.0 ST Arrays and images were processed to obtain probe intensities using standard procedures at the GTF (Gene Technology Facility, CIG, University of Lausanne). Background subtraction, RNA normalization and probeset summarization were performed using the Affymetrix Power Tools software package (Affymetrix CEL files). Sample correlation was performed on the top 1000 expressed probesets using Bioconductor affy and affyPLM packages in R. The microarray data from this publication have been recorded into the GEO database http://www.ncbi.nlm.nih.gov/geo/info/linking.html and assigned the identifier GSE34559.

Survival Analysis

Publicly available normalized expression data from 1809 breast cancer patients was downloaded from http://kmplot.com. For the relapse free survival analysis we selected lowest and highest expression values of 205572_at, 209652_s_at and 201743_at probes, corresponding with ANG-2, PlGF and CD14 genes respectively, using as threshold the first and third quartile respectively. To generate the Kaplan-Meier plots and to evaluate the separation between groups (log-rank statistic) we used the survival package in R.

Results

TIE-2 and VEGFR Pathways Control TEM Pro-Tumoral Activities and the TEM Reversion of TEM into Immunological Potent Monocytes.

Breast Tumor TEM are Pro-Angiogenic Suppressive Monocytes.

Angiogenesis plays a key role in tumor growth and cancer progression. TIE-2-expressing monocytes (TEM) have been reported to critically account for tumor vascularization and growth in mouse tumor experimental models (DePalma et al., 2005; Venneri et al., 2007), but the molecular basis of their pro-angiogenic activity are largely unknown. Moreover, differences in the pro-angiogenic activity between blood circulating and tumor infiltrated TEM in human patients has not been established to date, hindering the identification of specific targets for therapeutic intervention.

TEM isolated from breast cancer patient peripheral blood or tumor tissue were injected in the cornea of immunocompromised mice. The cornea itself is avascular and was injected with TEM isolated from patient peripheral blood and tumor tissue. Thus, any growth of new vessels from the peripheral limbal vasculature must be due to injected TEM and reflect their pro-angiogenic activity. We show that, in breast cancer patients the pro-angiogenic activity of TEM increased drastically from blood to tumor (FIG. 1A) suggesting that the tumor microenvironment shapes the highly pro-angiogenic phenotype of TEM. Tumor TEM are paracrine inducers of tumor angiogenesis by releasing high levels of angiogenic factors (i.e. VEGF, bFGF, and ANG-1) and MMP9 (matrix metalloproteinase 9) (FIG. 1B). They display mixed M1-like (tumor-associated macrophages releasing inflammatory molecules) and M2-like (immunosuppressive macrophages polarized by anti-inflammatory molecules) phenotype, with secretion of both the pro- and anti-inflammatory cytokines IL-12 and IL-10, respectively (FIG. 1B). We show that TEM are suppressive cells (Ibberson et al., 2013) consistent with their secretion of immunosuppressive cytokines such as VEGF and IL-10 (FIG. 1C). Finally, the vast majority of tumor TEM (>95%) express larger levels of TIE-2 (receptor of Ang-1 and Ang-2) and VEGFR-1 (receptor of PlGF and VEGF) relative to their blood counterparts (FIG. 1C).

TIE-2 and VEGFR Pathways Synergistically Control TEM Pro-Angiogenic Activity.

Given that TEM circulating in the blood infiltrate tumor tissue where they further differentiate our data suggest that the tumor microenvironment shapes their highly pro-angiogenic phenotype. By combining Boolean modelling and experimental approaches, we predicted in silico all minimal perturbations transitioning the highly pro-angiogenic phenotype of tumor TEM to the weak pro-angiogenic phenotype of blood TEM and vice versa. This goal was achieved by constructing an integrative and predictive model of TEM behavior based on experimental data (Guex et al., 2014, manuscript attached to this application). This model was interrogated to identify combined treatments that would alter TEM pro-angiogenic activity (Table 1).

Quite remarkably, four of the five predicted treatments (boxed in Table 1) that we validated experimentally proved to be extremely efficient at inhibiting or promoting tumor TEM proangiogenic activity experimentally (Guex et al., 2014, manuscript attached to this application). Examples of treatments validated using patient TEM isolated from tumor or peripheral blood are shown in FIG. 2. These treatments resulted in altered angiogenic activity (FIGS. 2A and B), and shifted TEM paracrine secretion profile (FIG. 2C) and consistently modulated the expression of TIE-2 and VEGFR-1 (FIG. 2D). Of note, TIE-2 and VEGFR kinase inhibitors when combined, but not when alone, drastically impaired tumor TEM pro-angiogenic activity as measured by Human Vascular Endothelial Cell sprouting assay (FIG. 2B). These data show that TIE-2 and VEGFR kinase activities synergistically control TEM pro-angigoenic activity. Finally, combined used of TNF-α, TGF-β and PlGF (Table 1, group 3) also significantly reduced TEM pro-angiogenic activity but not more than 60%.

Computationally predicted minimal treatments required for transitioning TEM into highly or weakly pro-angiogenic monocytes. These two final desired cell steady states were obtained by assigning in the TEM model to TIE-2 and VEGFR-1 nodes a fixed polarity of either both high (highly pro-angiogenic i.e tumor TEM) or low (weakly proangiogenic i.e. blood TEM) expression levels (Guex et al., 2014, manuscript attached to this application). Treatments decreasing TEM pro-angiogenic activity were classified in three groups based on the receptor tyrosine kinase inhibited and inflammatory (TGF-β or TNF-α) and angiogenic ligands up-regulated. Treatments validated experimentally are boxed.

TABLE 1

|  |  | RTK activity inhibited | Up-regulated Inflammatory Ligand | Up-regulated VEGFR-1 ligand | Up-regulated TIE-2 ligand |
|---|---|---|---|---|---|
| Transition to weakly pro-angiogenic TEM | | | | | |
| | Group 1 | TIE-2 | TGF-β | VEGF | - |
| | | TIE-2 | TGF-β | PlGF | - |
| | Group 2 | TIE-2 | TGF-β | - | ANG-1 |
| | | TIE-2 | TGF-β | - | ANG-2 |
| | | VEGFR-1 | TNF-α | - | ANG-1 |
| | | VEGFR-1 | TNF-α | VEGF | - |
| | | VEGFR-1 | - | all but PlGF | - |
| | Group 3 | TIE-2 and VEGFR-1 | - | - | - |
| | | - | TNF-α and TGF-β | PlGF | - |
| | | - | TNF-α and TGF-β | - | ANG-1 |
| | | - | TNF-α and TGF-β | VEGF | - |
| Transition to weakly pro-angiogenic TEM | | - | TNF-α | PlGF | ANG-2 |

Anti-Angiogenic Treatments Reverse TEM into Immunological Potent Monocytes

Treatments inhibiting TEM pro-angiogenic activity down-modulated and simultaneously up-regulated the expression of pro-angiogenic and anti-angiogenic genes, respectively (FIG. 3A). In response to these treatments, 95% of the genes functionally related to the cell cycle displayed a down-modulated expression indicating that TEM stopped proliferating with profound changes in their metabolism but without, however undergoing apoptosis. Further, TEM down-modulated the expression of genes involved in macrophage differentiation and started to acquire the profile of myeloid dendritic cells (FIG. 3A and Ibberson et al, 2013). Along these lines, genes encoding for dendritic cell markers, antigen processing and adaptive immune response were up-regulated while genes involved in immune suppression show markedly decreased expression (FIG. 3A and Ibberson et al., 2013). Finally the expression of genes related to adhesion and migration were up- and down-regulated respectively indicating that TEM mobility was strongly reduced; an observation consistent with the arrest of their cell cycle and the alteration of their differentiation program. Taken together, our results suggest that anti-angiogenic treatments shifted the gene expression profile of TEM toward the one of cells promoting immune surveillance, thereby limiting tumor growth (Guex et al., 2014, supplemental data, manuscript attached to this application). Most importantly, these data show that tumor TEM are plastic cells and can be reverted to immunological potent monocytes.

Finally, consistent with a synergy between TIE-2 and VEGFR signaling axes to control TEM pro-angiogenic activity (FIG. 2B), a relapse free survival analysis showed a statistically significant difference between patients with tumors with high and low expression values for genes encoding for CD14, Ang-2 and PlGF (FIG. 3B).

TILs can Expand from Breast Tumor Fragments Treated with TIE-2 and VEGFR Kinase Inhibitors.

Treatment of Breast Tumor Tissue Fragments with TIE-2 and VEGFR Kinase Inhibitors Allows TIL Expansion.

In contrast to other cancer types, Adoptive T-cell therapy (ACT) is still not a treatment modality in breast cancer. Very few studies have reported TIL expansion from breast cancer tissue and the corresponding expanded TILs show no to weak killing potential and lack of specificity (Schwartzentruber D J et al., 1992; Baxevanis C N et al., 1994). The generation of autologous T cells ex-vivo for ACT consists in the expansion of T cells from tumor biopsies in the presence of high doses of cytokines (IL-2 or IL-7/15) for 21 days followed by a Rapid Expansion Protocol (REP) consisting of two weeks of culture of the obtained TILs in the presence of allogenic irradiated feeder cells (peripheral blood mononuclear cells), anti-CD3 stimulating antibodies and lower doses of IL-2 (Dudley M E et al., 2003 and FIG. 4).

A main obstacle to the expansion of functional TILs from breast cancer tissue might be infiltration of breast tumor by a large number of immunosuppressive pro-angiogenic TEM. Hence, TIL expansion from breast cancer tissue may require an intervention that goes beyond IL-2-mediated T cell activation and overcomes breast cancer immune suppression. Based on our observations on TEM (see previous section), combined use of TIE-2 and VEGFR kinase inhibitors emerged a possible relevant intervention to restore monocytes and T cell functions and to expand TILs ex vivo.

Thus, 4-6 mm$^3$ breast tumor tissue fragments ex-vivo from breast cancer patients either obtained fresh or cryo-preserved were treated with 10 μM of TIE-2 and VEGFR kinase inhibitors for 12 hours in RPMI medium supplemented with 10% FCS or 10% human serum. Each fragment was washed three times in 0.2 ml of RPMI containing 10% serum for 5 min and placed into a 24 well plate in the presence of high doses IL-2 (6000 U/ml) or IL-7 and IL-15 (10 ng/ml each) for 21 days. The culture medium is changed twice a week by removing 65% of the medium and refilling the culture with the same volume of fresh medium. Of more than 120 individual fragment-derived cultures from 12 distinct tumors, 72% show robust expansion when treated with the kinase inhibitors while 31% of the untreated fragments showed TIL expansion (FIG. 5A), albeit to a lesser extent. After 21 days in culture 0.3 to 0.9 million T cells were obtained from a 4-6 mm$^3$ tumor tissue fragment treated with the kinase inhibitors.

Combining TIE-2 and VEGFR Kinase Inhibitors with TIL Attraction Out of the Tumor Tissue Fragment Increased the Frequency of CD137$^+$ TILs.

Three different TIL culture formats have been tested, a regular 24 well plate, a 24 transwell plate and a 24 transwell plate into which we placed into the lower compartment a 50 µl drop of matrigel containing 1 µg of CXCL-9 or CXCL-10 (FIG. 1B). Tumor fragments were first treated with TIE-2 and VEGFR kinase inhibitors as described above and placed in culture with IL-2 or IL-7 and IL-15 in different well formats. In the regular plate format, TILs expand in the same compartment as the tumor fragment and are largely exposed to inflammatory and suppressive molecules emanating for the tumor piece. By contrast, a transwell culture format allows TILs to expand in the lower compartment, away from the tumor piece. Since breast cancer TILs express at their surface large amounts of CXCR3 (the receptor of CXCL-9 and CXCL-10) they were strongly attracted by the chemokine gradient formed from the drop of gel. Thus, in a transwell format containing a chemokine gel, TILs migrate quickly from the breast tumor fragment to the lower compartment. Relative to a regular well format, a transwell format allowed a two-fold increase in the number of TILs obtained after 21 days. Relative to a regular well format, a transwell format containing a chemokine drop allowed a three- to four-fold increase in the number of TILs obtained after 21 days of culture. Importantly, efficient TIL expansion required pre-treatment of the tumor fragments with TIE-2 and VEGFR inhibitors independently of the culture format used.

CD4 and CD8 TILs obtained after 21 days of culture show a central memory/effector memory phenotype and express the inhibitory receptors PD-1, LAG3, TIM3 and BTLA (FIG. 1C). Roughly half of the expanded TILs expressed PD-1 (FIG. 5C). Less than 20% of the TILs expressed CD137$^+$ which recently emerged as a marker of tumor specific T cells in ovarian cancer (Ye et al., 2013). No significant change in this phenotype was obtained with the transwell culture format. However and most importantly, in the presence of the chemokine drop in the transwell, the frequency of CD137$^+$ TILs increased dramatically and reached 80%.

Expanded TILs Encompass a TSC$_M$ (Stem Cell Memory) Population.

A fraction of TILs (0.81+/−0.54%) display a stem cell memory phenotype T$_{SCM}$ (CD45RA$^+$, CD95$^+$, CD62L$^+$, CCR7$^+$, IL2R-β$^+$). T$_{SCM}$ is a long-lived memory T cell population that has been reported to show an enhanced capacity for self-renewal, a multipotent ability to derive central memory, effector memory and effector T cells and a superior aptitude to mediate anti-tumor response in a humanized mouse model (Gattitoni et al., Nature Medicine, 2011; Restifo and Gattitoni, Current opinion in immunology., 2013).

Triggering of CD28 and CD137 During the Rapid Expansion Protocol (REP) Allows the Expansion of Less Differentiated and More Efficient TILs TIL Expansion.

Figure 4:
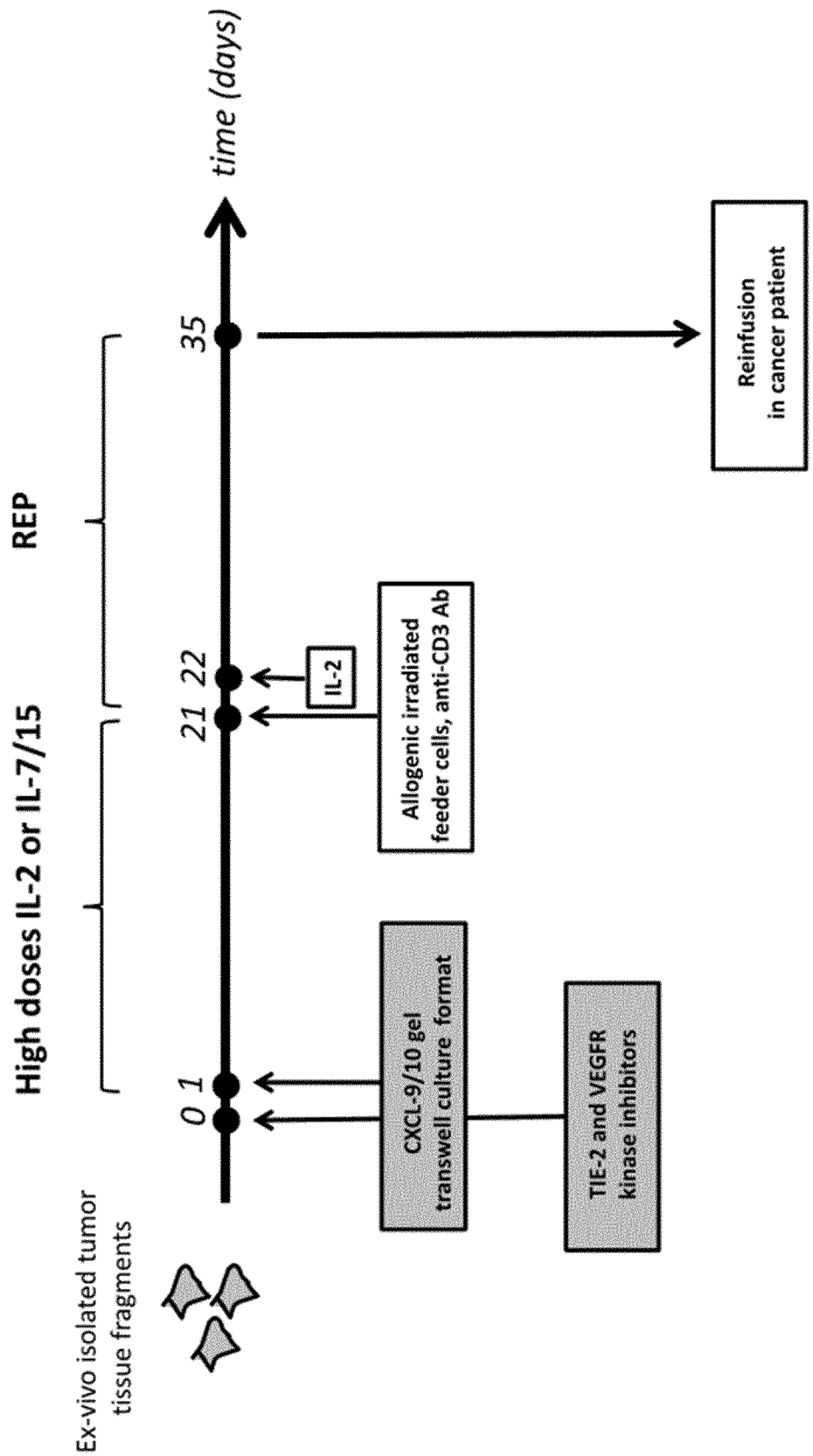
FIG. 4: Expansion of TILs for adoptive T cell therapy. Regular protocol of TIL expansion for adoptive T cell therapy. Ex-vivo isolated tumor specimens are processed in small fragments and placed in culture in the presence of high doses of cytokines (IL-2 or IL-7/15) for 21 days (TIL generation phase). The obtained TILs are then expanded through a REP (Rapid Expansion Protocol) during two weeks. The REP consists in expanding TILs using allogenic irradiated feeder cells and anti-TCR/CD3 antibodies (expansion phase). This procedure allows to obtain large amounts of TILs ($10^{10}$-$10^{11}$) which are re-infused in cancer patient. TIL function is usually measured by their aptitude to release IFN-γ in response to specific targets. The grey boxes indicate the changes, relative to the regular TIL expansion protocol, that allow the expansion of functional breast tumor TILs.

The rapid expansion protocol (REP) established for the expansion of melanoma TILs (Dudley M E et al., 2003) was used for breast cancer TILs. It consists in mixing TILs expanded from a tumor fragment at day 21 with irradiated allogenic PBMC (1:100 TIL to PBMC ratio) in the presence of 30 ng/ml of anti-CD3 antibody (OKT3). The next day IL-2 is added to the culture at 3000 U/ml. The medium is changed at day 5 and TILs are collected at day 14 (FIG. 4).

This procedure expanded CD8 and CD4 breast TILs (CD8/CD4 ratio=0.9±0.6) to comparable numbers obtained in melanoma by other groups (Dudley M E et al., 2003). Thus, from a single 4-6 mm$^3$ tumor tissue fragment and using a regular 24 well plate (FIG. 5B, top panel), 1±0.3 million TIL were obtained at day 21 which after REP led to 750±250 millions of TILs. Most importantly, using a 24 transwell format and a chemokine gel (FIG. 1B, bottom panel), three to four times more TILs were obtained at the end of the REP (2250-3000 millions of TILs/4-6 mm$^3$ tumor tissue fragment).

Expanded TILs Show an Effector Memory Phenotype and Kill Breast Tumor Cells In Vitro.

Relative to TILs obtained at day 21 (FIG. 5C), TILs obtained post-REP display a slightly different phenotype with CD4 TILs showing down-modulation of CD27. A significant fraction of pre-REP and post-REP TILs express TIM-3, LAG-3 and BTLA (FIG. 6A). The killing aptitude of TILs was assessed by chromium release assay using as target cells autologous tumor cells derived from the primary tumor according to a recently described method (Palechor-Ceron N et al., 2013). These TILs were functional as they specifically killed tumor cells in vitro in a MHC class I and Class II-dependent manner (FIG. 6B). Further, they also released IFN-γ in response to tumor cells in a MHC class I and Class II-dependent manner (FIG. 6C).

Expanded TILs Encompass a T$_{SCM}$ Population.

The TIL population expanded after REP encompassed a T$_{SCM}$ population independently of the modifications introduced in the culture format or in the REP.

Example 2

Material and Methods

Reagents.

Kinase inhibitors: TIE-2 and VEGFR kinase inhibitors were from Selleckchem and MedChem Express. TIE-2 and VEGFR IC50 are reported in the table below:

TABLE 3

| Inhibitor name | IC 50 TIE-2 | IC50 VEGFR | Additional inhibition reported |
|---|---|---|---|
| Compound 7 C26H21N3O2S, SB633825 | 0.3 µM | 0.25 µM VEGFR-2/3 (nd/nd) | p38, PDGFR1 |

TABLE 3-continued

| Inhibitor name | IC 50 TIE-2 | IC50 VEGFR | Additional inhibition reported |
|---|---|---|---|
| 4-(5-(6-methoxynaphthalen-2-yl)-2-(4-(methylsulfinyl)phenyl)-1H-imidazol-4-yl)pyridine | | | |
| Rebastinib (DCC-2036) | 3.4 nM | VEGFR-1/2 (12/34 nM) kinases | Abl, HCK and Src |
| PTK787 | | VEGFR-1/2 (77/37 nM) | c-Kit, PDGFR |
| Cabozantinib | 14.3 nM | VEGFR-1/2/3 (12/0.035/6 nM) | c-Met, Ret Kit, Flt-3, AXL |
| Tivozanib | | VEGFR-1/2/3 (30/6.15/15 nM) | PDGFR, c-Kit |
| Axitinib | | VEGFR-1/2/3 (0.1/0.2/0.3 nM) | PDGFR, c-Kit |
| Altiratinib (DCC-2701) | 2 nM | VEGFR-2 (4 nM) | Met |

All the inhibitors were applied to 1 mm3 tumor fragment at a concentration of 2×IC50 (indicated in bold in the table, nd: not determined) either alone or in combination for 12 hours at 37° C. in RPMI 1640 supplemented with 10% FCS. Based on previous experiments on human monocytes, Rebastinib, Altiratinib, PTK787 and compound 7 were used at 30 nM, 30 nM, 5 μM and 5 μM, respectively. The fragments were washed, placed in culture as previously described and 20 days later the number of T cells obtained were counted. Antibodies and multimers of MHC class I: antibodies specific for CD4, CD8, CD3 and CD28 were from Beckton Dikinson. Antibodies specific for PD-1 were from Affimetrix eBioscience (clone J105, PD-1 PerCP-eF710), anti-LAG-3 antibodies were from Enzo Life Science (clone 17B4, LAG-3-FITC), anti-CD137 antibodies were from Biolegend (clone 4B4-1, CD137-BV605). Fluorescently labelled Her2/neu MHC-classI multimers were from TCMetrix (Epalinges, Swizerland).

Analysis of T Cell Phenotype and Functions.

T cell phenotype was analyzed by flow cytometry using a Facs LSRII (BD Biosciences). T cell killing aptitude was assessed by chromium release assay (Rosato, 1999) using as target cells T2 (174×CEM.T2) cells pulsed with the Her2/neu tumor antigenic peptide.

Experimental Mouse Model of Breast Cancer.

1×106 168FARN cells were orthotopically transplanted into the inguinal mammary fat pad of 10-week-old BALB/cJ mice. When the tumor reached a volume of 50 mm3, mice were injected intra-tumorally 4 times every other day with PBS (control group) or with 45 ng of PTK787 and Compound 7 (treated group). Tumor size was monitored with a caliper, the treated tumors kept a well-defined measurable shape until day 16 post-treatment at which point measurements became impossible as the tumor mass was not clearly palpable anymore in the treated group. The mice were sacrificed 3 weeks after the last injection. Tumors were collected in OCT and 5 μm sections of frozen OCT tumors were stained with Alexa647 conjugated anti-CD31 antibodies, FITC-conjugated anti-Ki67 antibodies and Dapi. The labelled sections were examined by confocal microscopy and the cell proliferation measured as the ratio of K167 to Dapi signals. Tumor blood vessel density was measured as the ratio of CD31 signal to the tumor surface area. Mouse spleens were collected, dissociated freshly, stained for CD3, CD4 and FOXP-3 antibodies and analyzed by low cytometry. The fraction of regulatory T cells was calculated as number of CD3+CD4+FOXP3+ cells amongst CD3+CD4+ cells. The proliferative capacity of T cells in control and treated mice was evaluated in vitro in a co-culture assay. Briefly, T cells and CD11c dendritic cells were isolated from the spleen by immunomagnetic selection. T cells were labelled with the fluorescent cell tracker carboxyfluorescein succinimidyl ester (CFSE) and co-cultured for 5 days with CD11c cells in the presence or absence of a cell extract of 168FARN cells. 168FARN cell extract was used as a source of tumor antigens which are presented by CD11c dendritic cells to T cells. The extract was obtained by exposure of a culture of 168FARN to freezing/thawing cycles and by sonication of this material. The T cell proliferative capacity was measured as a ratio as follows: (fraction of proliferating T cells (CFSE low) in the presence of the tumor cell extract)/(fraction of proliferating T cells (CFSE low) in the absence of the tumor cell extract).

Results

Inhibitors of TIE-2 and VEGFR Allow T Cell Expansion from Breast Cancer Fragments.

Significant expansion of T cells was obtained following overnight treatment of breast tumor fragments with kinase inhibitors of TIE-2 and VEGFR. Importantly while all these inhibitors block TIE-2 and VEGFR with different affinities and specificities (see table under material and methods section), they display various efficiency to induce T cell expansion in the presence of high doses IL-2 (FIG. 7). Importantly, no T cell expansion was obtained in the absence of kinase inhibitor and in the presence of high doses IL-2. The most efficient kinase inhibitor treatments for T cell expansion was PTK787 together with compound 7 and 4-(5-(6-methoxynaphthalen-2-yl)-2-(4-(methylsulfinyl)phenyl)-1H-imidazol-4-yl)pyridine alone. These two treatments resulted in the expansion of more than one million of T cells per 1 mm3 of breast tumor tissue over the first 20 days of culture. In contrast to compound 7 and Rebastinib, 4-(5-(6-methoxynaphthalen-2-yl)-2-(4-(methylsulfinyl)phenyl)-1H-imidazol-4-yl)pyridine inhibitor targets both TIE-2 and VEGFR quite selectively which may explain its efficiency when used alone (FIG. 7).

Expanded Breast Cancer CD8 TILs are Functional Tumor-Specific Cells which Display High Levels of Expression of CD137, CD28 and BTLA.

Figure 8:
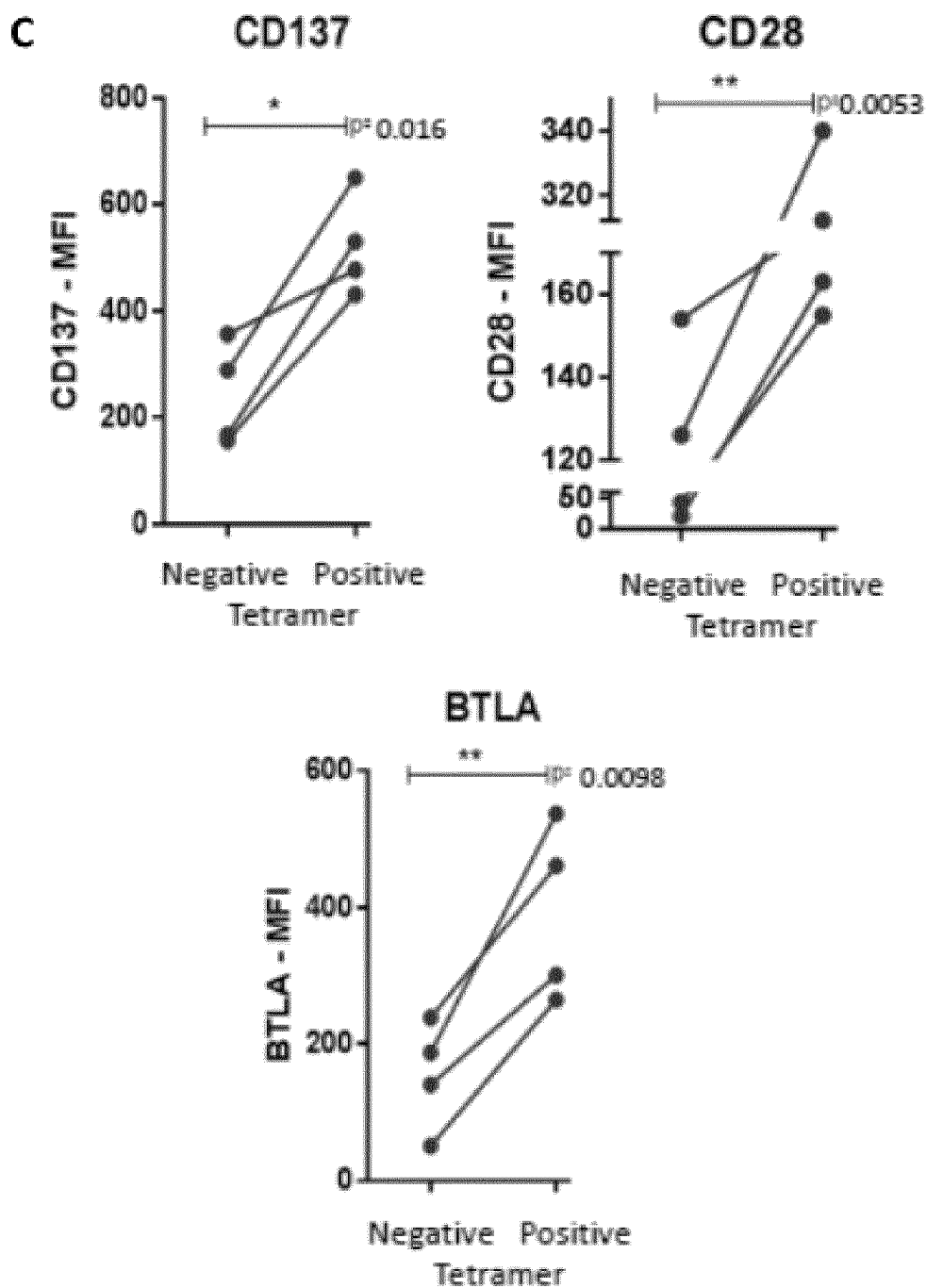
FIG. 8: Tumor-specific TILs expanded in vitro are able to kill tumor cells and display a specific phenotype. A) Expansion of tumor-specific CD8 T cells in vitro during the time course of TIL expansion (primary tumor: day 0, end of generation phase: day 21, end of expansion phase: day 35). CD8 T cells were stained with multimeric MHC class I complexes displaying Her2/neu tumor antigenic peptide and their frequency quantified by Facs. Shown are the expansions of four TIL cultures from four distinct tumors. B) Expanded CD8 T cells kill T2 cells pulsed with Her2/neu tumor-specific antigen. C) Tumor-specific CD8T cells, which stain positively for tumor antigen multimers, display a specific phenotype characterized by an increased expression of CD137, CD28 and BTLA.

In order to assess the expansion of tumor-specific T cells, we stain the expanded TILs at different time of the culture using multimeric MHC class I molecules specific for various breast tumor antigens (Her2/neu, WT1, NY Br1 and p53). The frequency of tumor-specific TILs in the primary tumor was consistently low and detected following enzymatic digestion of a small fraction of the primary tumor. Further, we observed a dramatic expansion of Her2/neu-specific CD8 T cells during the generation and the expansion phase (FIG. 8A). Importantly, the expanded TILs were able to kill in vitro T2 target cells pulsed with the corresponding Her2/neu tumor antigenic peptide. This killing activity was MHC-dependent and abrogated by function blocking antibodies specific for MHC-Class I molecules (FIG. 8B). Finally, relative to non-tumor-specific TILs, Her2/neu tumor-specific CD8 TILs display a different phenotype with high expression levels of CD28, CD137 (4-1BB) and BTLA (FIG. 8C). These results suggest that high expression levels of these receptors at the surface of breast cancer TILs might be used as a signature for tumor-specific TILs.

TIE-2 and VEGFR Kinase Inhibitors Induced Tumor Reduction and Enhanced Anti-Tumor T Cell Response in a Mouse Experimental Model of Breast Cancer.

Figure 9:
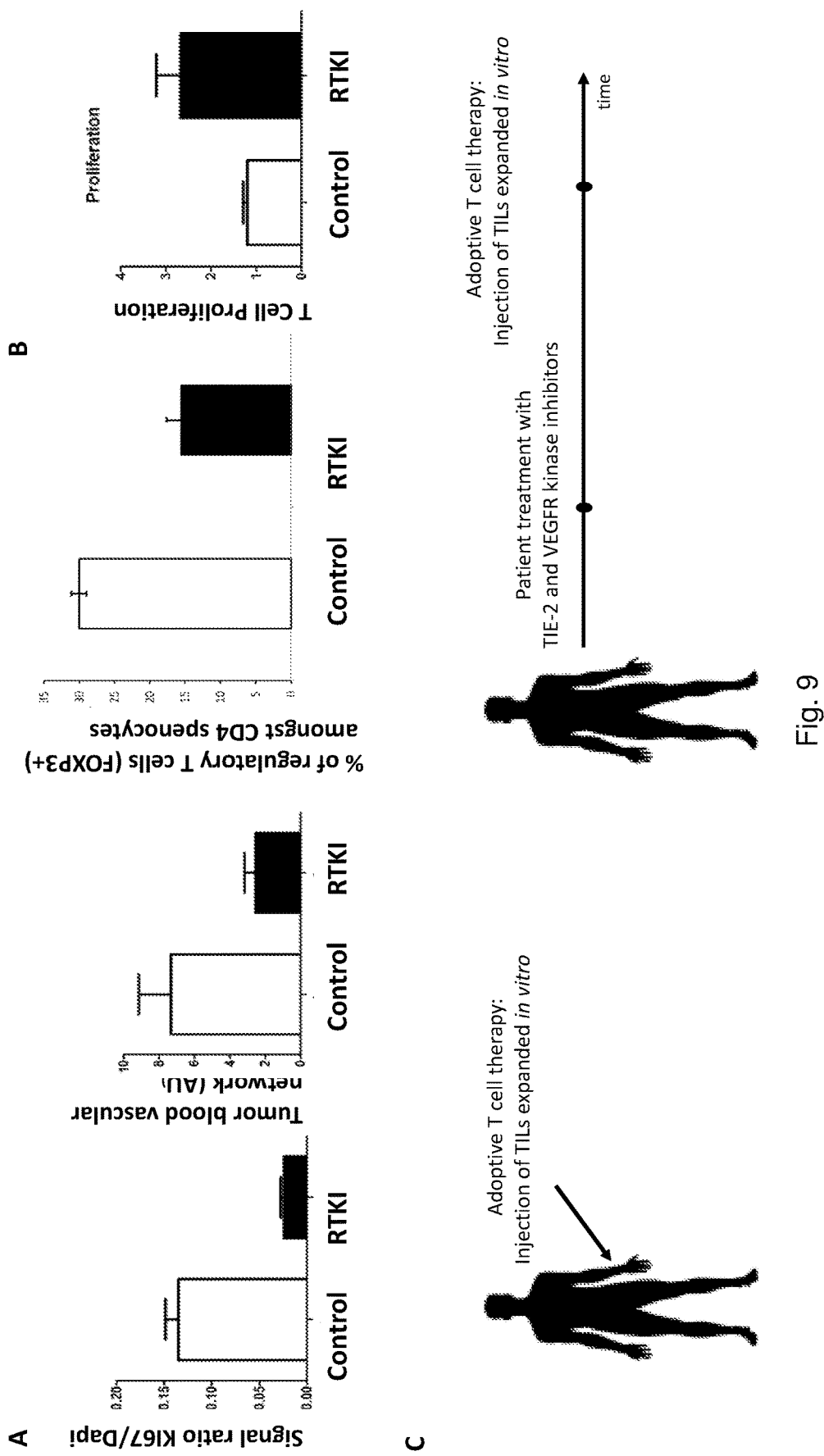
FIG. 9: In vivo treatments. A) Response of mice bearing orthotopic 168FARN mammary tumors following intratumoral injection with TIE-2 and VEGFR kinase inhibitors. Quantification by confocal microscopy in sections of mouse tumors of cell proliferation (K167/Dapi, left panel) and tumor blood vascular network (AU: arbitrary units, middle panel) 16 days post-treatment. The percentage of regulatory T cells (FOXP3+ cells amongst CD4 cells, right panel) was quantified in CD4 T splenocytes in treated and untreated mice 16 days post-treatment. B) Evaluation in vitro of the anti-tumor response of T cells isolated from the spleen of treated and untreated mice. T cells were stained with CFSE, co-cultured with tumor cells and the fraction of proliferating T cells evaluated by Facs. Shown is the fold increased in proliferating T cells in the presence and in the absence of tumor cells. C) Strategy of treatment of breast cancer patient using either T cell-based adoptive therapy alone (left panel) or following treatment of the patient with kinases inhibitors targeting TIE-2 and VEGF signaling axes.

Consistent with our previous studies reporting the synergistic action of TIE-2 and VEGFR on TEM suppressive and angiogenic activities (Ibberson et al., 2013; Guex et al., 2015), we observed that the inhibition of the kinase activity of these receptors induced a significant reduction of the growth of 168FARN tumor in an orthotopic model of breast cancer. 168FARN tumors induce metastasis to the lymph node but not to distant organs. 50 mm3 tumors were treated by four intratumoral injections every other day of TIE-2 and VEGFR kinase inhibitors. 16 days post-treatment, treated mice had no longer palpable tumors while untreated mice show 120 mm$^3$ tumors. Mice were sacrificed at three weeks post-treatment and remaining small non-palpable tumors were collected in treated mice. Tumors from treated and untreated mice were characterized as well as their tumor-specific T cell responses. Cell proliferation, as measured by K167 staining, was strongly reduced in the tumors of treated mice relative to untreated mice (FIG. 9A, left panel). Similarly, the density of the tumor blood vascular network was significantly lower in treated mice (middle panel) as well as the frequency of regulatory T cells in their spleen (right panels). Further, tumor-specific T cell responses were examined in vitro in a co-culture assay using purified T cells from the spleen and 168FARN tumor cells expanded in vitro. T cells were previously labelled with CFSE to assess their proliferative capacity. A significant increase in the proliferation of T cells isolated from treated mice was observed relative to treated mice (FIG. 93B). Taken together, these results indicate that TIE-2 and VEGFR kinase inhibitor treatment induced a reduction of the tumor growth associated with a decreased tumor vascularization and an enhanced anti-tumor T cell response. This combined kinase inhibitor treatment did not induce full regression of the tumors and might be synergistic when combined with adoptive T cell therapy (FIG. 9C). Indeed, this combined kinase inhibitor treatment alleviates tumor immune suppression (FIG. 9B) and thus is expected to potentiate T cell-based adoptive cell therapy. Hence, two treatment modalities are envisioned: adoptive T cell therapy alone (FIG. 9C, left panel) or subsequent to the treatment of patients with TIE-2 and VEGFR kinase inhibitors (FIG. 9C, right panel).

REFERENCES

Auerbach R, Lewis R, Shinners B, Kubai L, Akhtar N (2003) Angiogenesis assays: a critical overview. Clin Chem 49: 32-40.
Baxevanis C N, Dedoussis G V, Papadopoulos N G, Missitzis I, Stathopoulos G P, Papamichail M. Cancer. Tumor specific cytolysis by tumor infiltrating lymphocytes in breast cancer. 1994 Aug. 15; 74(4):1275-82.
Chacon J A, Wu R C, Sukhumalchandra P, Molldrem J J, Sarnaik A, Pilon-Thomas S, Weber J, Hwu P, Radvanyi L. Co-stimulation through 4-1BB/CD137 improves the expansion and function of CD8(+) melanoma tumor-infiltrating lymphocytes for adoptive T-cell therapy. PLoS One. 2013; 8(4):e60031.
De Palma M, Venneri M A, Galli R, Sergi Sergi L, Politi L S, et al. (2005) Tie2 identifies a hematopoietic lineage of proangiogenic monocytes required for tumor vessel formation and a mesenchymal population of pericyte progenitors. Cancer Cell 8: 211-226.
Dudley M E, Wunderlich J E, Shelton T E, Even J, Rosenberg S A. Generation of Tumor-Infiltrating Lymphocyte Cultures for Use in Adoptive Transfer Therapy for Melanoma Patients. J Immunotherapy. 2003; 26(4): 332-342.
Gattinoni L, Lugli E, Ji Y, Pos Z, Paulos C M, Quigley M F, Almeida J R, Gostick E, Yu Z, Carpenito C, Wang E, Douek D C, Price D A, June C H, Marincola F M, Roederer M, Restifo N P. A human memory T cell subset with stem cell-like properties. Nat Med. 2011 Sep. 18; 17(10):1290-7.
Ibberson M, Bron S, Guex N, Faes-van't Hull E, Ifticene-Treboux A, Henry L, Lehr H A, Delaloye J F, Coukos G, Xenarios I, Doucey M A. TIE-2 and VEGFR kinase activities drive immunosuppressive function of TIE-2-expressing monocytes in human breast tumors. Clin Cancer Res. 2013 Jul. 1; 19(13):3439-49.
Korff T, Augustin H G (1999) Tensional forces in fibrillar extracellular matrices control directional capillary sprouting. J Cell Sci 112 (Pt 19): 3249-3258.
Palechor-Ceron N, Suprynowicz F A, Upadhyay G, Dakic A, Minas T, et al. Radiation induces diffusible feeder cell factor(s) that cooperate with ROCK inhibitor to conditionally reprogram and immortalize epithelial cells. Am J Pathol (2013). 183: 1862-1870.
Restifo and Gattinoni. Lineage relationship of effector and memory T cells. Curr Opin Immunol. 2013 October; 25(5):556-63.
Rosato, A., G. Milan, D. Collavo, P. Zanovello. DNA-based vaccination against tumors expressing the P1A antigen. Methods. 1999 19: 187-190.
Schwartzentruber D J, Topalian S L, Manicini M, Rosenberg S A. Characterization of lymphocytes infiltrating human breast cancer: specific immune reactivity detected by measuring cytokine secretion. J Immunother 1992; 12:1-12.
Venneri M A, De Palma M, Ponzoni M, Pucci F, Scielzo C, et al. (2007) Identification of proangiogenic TIE2-expressing monocytes (TEMs) in human peripheral blood and cancer. Blood 109: 5276-5285.
Wolfl M, Kuball J, Ho W Y, Nguyen H, Manley T J, Bleakley M, Greenberg P D. Activation-induced expression of CD137 permits detection, isolation, and expansion of the full repertoire of CD8+ T cells responding to antigen without requiring knowledge of epitope specificities. Blood. 2007 Jul. 1; 110(1):201-10.
Ye Q, Song D, Poussin M, Yamamoto T, Best A, Li C, Coukos G, Powell D. J. CD137 accurately identifies and enriches for naturally-occurring tumor-reactive T cells in tumor. Clinical Cancer Research, 2013; 20(1), 44-55.

The invention claimed is:
1. A pharmaceutical composition comprising a therapeutically effective number of breast cancer specific TILs produced and/or expanded ex vivo by i) obtaining one or more tumor fragments from a patient in need of cancer treatment,
ii) contacting said one or more tumor fragments with a TIE-2 and a VEGFR kinase inhibitor,
iii) culturing said one or more tumor fragments in the presence of one or more growth promoting substances,
iv) expanding said TILs, and
v) recovering the expanded TILs.

2. The pharmaceutical composition of claim 1, wherein the expanded recovered breast cancer specific TILs are CD4 and/or CD8.

3. The pharmaceutical composition of claim 2, wherein the breast cancer specific TILs are CD8 that express high levels of CD137, CD28 and BTLA.

4. The pharmaceutical composition of claim 2, wherein the CD4 and/or CD8 display a stem cell memory phenotype (TSCM).

5. The pharmaceutical composition of claim 1, further comprising a therapeutically effective amount of a cytokine selected from the group consisting of a chemokine, an interleukin, an interferon (IFN-α or IFN-δ) and a combination of two or more of these cytokines.

6. The pharmaceutical composition of claim 5, wherein the interleukin is selected from the group consisting of interleukin-2, interleukin-4, interleukin-6, interleukin-7, interleukin-12, interleukin-15, interleukin-21, a functionally similar interleukin, and a combination of two or more of these interleukins.

7. A kit comprising
a pharmaceutical composition comprising a therapeutically effective number of breast cancer specific TILs produced and/or expanded ex vivo by
i) obtaining one or more tumor fragments from a patient in need of cancer treatment,
ii) contacting said one or more tumor fragments with a TIE-2 and a VEGFR kinase inhibitor,
iii) culturing said one or more tumor fragments in the presence of one or more growth promoting substances,
iv) expanding said TILs, and
v) recovering the expanded TILs.

* * * * *